US006472162B1

(12) United States Patent
Coelho et al.

(10) Patent No.: US 6,472,162 B1
(45) Date of Patent: Oct. 29, 2002

(54) METHOD FOR PREPARING THROMBIN FOR USE IN A BIOLOGICAL GLUE

(75) Inventors: Philip Henry Coelho, El Dorado Hills; Phil Kingsley; Jim Brausch, both of Sacramento; James H. Godsey, Folsom, all of CA (US); Gail Rock, Ottawa (CA); Trista K. Madsen, Elk Grove; Sona B. Frausto, Sacramento, both of CA (US)

(73) Assignee: ThermoGenesis Corp., Rancho Cordovo, CA (US)

( * ) Notice: Subject to any disclaimer, the term of this patent is extended or adjusted under 35 U.S.C. 154(b) by 0 days.

(21) Appl. No.: 09/328,350

(22) Filed: Jun. 4, 1999

(51) Int. Cl.$^7$ ................................................ C12Q 1/56

(52) U.S. Cl. .................. 435/13; 424/94.64; 514/21; 604/6

(58) Field of Search ................... 210/782; 422/101; 424/94, 64; 435/13, 2; 514/21; 530/382; 604/6

(56) References Cited

U.S. PATENT DOCUMENTS

| | | |
|---|---|---|
| 713,017 A | 11/1902 | Pumphrey |
| 1,614,532 A | 1/1927 | Mobley |
| 2,533,004 A | 12/1950 | Ferry et al. |
| 2,747,936 A | 5/1956 | Wahlin |
| 3,179,107 A | 4/1965 | Clark |
| 3,223,083 A | 12/1965 | Cobey |
| 3,236,457 A | 2/1966 | Kennedy et al. |
| 3,269,389 A | 8/1966 | Meurer et al. |
| 3,416,737 A | 12/1968 | Venus, Jr. |
| 3,467,096 A | 9/1969 | Horn |
| 3,828,980 A | 8/1974 | Creighton et al. |
| 3,942,725 A | 3/1976 | Green |
| 3,945,574 A | 3/1976 | Polnauer et al. |
| 4,040,420 A | 8/1977 | Speer |
| 4,067,333 A | 1/1978 | Reinhardt et al. |
| 4,109,653 A | 8/1978 | Kozam et al. |
| 4,265,233 A | 5/1981 | Sugitachi et al. |
| 4,298,598 A | 11/1981 | Schwarz et al. |
| 4,359,049 A | 11/1982 | Redl et al. |
| 4,362,567 A | 12/1982 | Schwarz et al. |
| 4,363,319 A | 12/1982 | Altshuler |
| 4,374,830 A | 2/1983 | Schneider |
| 4,377,572 A | 3/1983 | Schwarz et al. |
| 4,414,976 A | 11/1983 | Schwarz et al. |
| 4,427,650 A | 1/1984 | Stroetmann |
| 4,427,651 A | 1/1984 | Stroetmann |
| 4,442,655 A | 4/1984 | Stroetmann |
| 4,453,939 A | 6/1984 | Zimmerman et al. |
| 4,627,879 A | 12/1986 | Rose et al. |
| 4,631,055 A | 12/1986 | Redl et al. |
| 4,655,211 A | 4/1987 | Sakamoto et al. |
| 4,696,812 A | 9/1987 | Silbering et al. |
| 4,714,457 A | 12/1987 | Alterbaum |

(List continued on next page.)

FOREIGN PATENT DOCUMENTS

| | | |
|---|---|---|
| CH | 259254 | 6/1949 |
| DE | 25913 | 2/1884 |
| EP | 0 443 724 A1 | 8/1991 |
| EP | 0 505 604 A1 | 9/1992 |
| EP | 0 534 178 A2 | 3/1993 |
| EP | 592242 | 4/1994 |
| SU | 1527261 A1 | 12/1989 |
| WO | WO 86/01814 | 3/1986 |
| WO | WO 88/02259 | 4/1988 |
| WO | WO 88/03151 | 5/1988 |
| WO | WO 91/09641 | 7/1991 |
| WO | WO 93/19805 | 10/1993 |
| WO | WO 94/05566 | 1/1994 |
| WO | WO 96/17871 | 6/1996 |
| WO | WO 96/31245 | 10/1996 |
| WO | WO 99/45938 | 9/1999 |

OTHER PUBLICATIONS

Fenton, J., "Human Thrombins", Chemistry & Biology of Thrombin, pp. 43–70. No dates given.
Rosenberg, R.D., et al., "Bovine Thrombin: Constant Specific Activity Products From Single Animals", Fed. Proc., p. 321, Abstract No. 361. No dates given.
Quick, A.J., "Production Of Thrombin From Precipitate Obtained By Acidification Of Diluted Plasma", pp. 114–118. No dates given.
Eagle, H., "Studies On Blood Coagulation", pp. 531–545, 1934.
Mann, K.G., et al., "The Molecular Weights Of Bovine Thrombin And Its Primary Autolysis Products", pp. 6555–6557, 1969.
Mann, K.G., et al., "Multiple Active Forms Of Thrombin", The Journal of Biological Chemistry, vol. 246(19), pp. 5994–6001, 1971.
Martin, M., et al., "Thrombolysis In Patients With Chronic Arterial Occlusions", Thrombolytic Therapy, vol. 47, pp. 235–241, 1971.
Fenton, J., et al., "Large–Scale Preparation And Preliminary Characterizations Of Human Thrombin", Biochimica et Biophysica Acta. vol. 229, pp. 26–32, 1971.
Andrianova, et al., "An Accessible Method Of Simultaneous Production Of Fibrinogen And Thrombin From Blood", pp. 648–650, 1975. (Plus English translation).

(List continued on next page.)

*Primary Examiner*—Ralph Gitomer
(74) *Attorney, Agent, or Firm*—Bernhard Kreten

(57) ABSTRACT

A sterile method for preparing stable thrombin component from a single donor's plasma in which the thrombin component and the clotting and adhesive proteins component are harvested simultaneously from the same donor plasma in less than one hour. The combined components provide an improved biological hemostatic agent and tissue sealant by virtue of its freedom from the risk of contaminating viruses or bacteria from allogenic human or bovine blood sources. The thrombin provides polymerization of the clotting and adhesive proteins in less than five seconds, and is sufficiently stable to provide that fast clotting over a six hour period. Further, the clotting times can be predictably lengthened by diluting the thrombin with saline.

119 Claims, 9 Drawing Sheets

U.S. PATENT DOCUMENTS

| | | |
|---|---|---|
| 4,734,261 A | 3/1988 | Koizumi et al. |
| 4,735,616 A | 4/1988 | Eibl et al. |
| 4,752,466 A | 6/1988 | Saferstein et al. |
| 4,767,416 A | 8/1988 | Wolf et al. |
| 4,826,048 A | 5/1989 | Skorka et al. |
| 4,842,581 A | 6/1989 | Davis |
| 4,874,368 A | 10/1989 | Miller et al. |
| 4,902,281 A | 2/1990 | Avoy |
| 4,909,251 A | 3/1990 | Seelich |
| 4,923,815 A | 5/1990 | Tanaka et al. |
| 4,965,203 A | 10/1990 | Silbering et al. |
| 4,978,336 A | 12/1990 | Capozzi et al. |
| 4,979,942 A | 12/1990 | Wolf et al. |
| 4,987,336 A | 1/1991 | L'Hermite et al. |
| 5,037,390 A | 8/1991 | Raines et al. |
| 5,089,415 A | 2/1992 | La Duca |
| 5,099,003 A | 3/1992 | Koitschke et al. |
| 5,104,375 A | 4/1992 | Wolf et al. |
| 5,116,315 A | 5/1992 | Capozzi et al. |
| 5,130,244 A | 7/1992 | Nishimaki et al. |
| 5,143,838 A | 9/1992 | Kraus et al. |
| 5,151,355 A | 9/1992 | Crowley et al. |
| 5,165,928 A | 11/1992 | Knighton |
| 5,185,001 A | 2/1993 | Galanakis |
| 5,219,328 A | 6/1993 | Morse et al. |
| 5,232,024 A | 8/1993 | Williams |
| 5,290,259 A | 3/1994 | Fischer |
| 5,290,552 A | 3/1994 | Sierra et al. |
| 5,304,372 A | 4/1994 | Michalski et al. |
| 5,328,462 A | 7/1994 | Fischer |
| 5,368,563 A | 11/1994 | Lonneman et al. |
| 5,393,666 A | 2/1995 | Linnau |
| 5,405,607 A | 4/1995 | Epstein |
| 5,411,885 A | 5/1995 | Marx |
| 5,443,959 A | 8/1995 | Kikuchi et al. |
| 5,460,945 A | 10/1995 | Springer et al. |
| 5,474,540 A | 12/1995 | Miller et al. |
| 5,474,770 A | 12/1995 | Broly et al. |
| 5,480,378 A | 1/1996 | Weis-Fogh et al. |
| 5,506,127 A | 4/1996 | Proba et al. |
| 5,510,102 A | 4/1996 | Cochrum |
| 5,575,779 A | 11/1996 | Barry |
| 5,578,459 A | 11/1996 | Gordon et al. |
| 5,585,007 A * | 12/1996 | Antanavich et al. ........ 210/782 |
| 5,605,887 A | 2/1997 | Pines et al. |
| 5,614,204 A | 3/1997 | Cochrum |
| 5,631,019 A | 5/1997 | Marx |
| 5,643,192 A * | 7/1997 | Hirsh et al. ..................... 604/4 |
| 5,646,265 A | 7/1997 | Epstein |
| 5,750,657 A | 5/1998 | Edwardson et al. |
| 5,795,571 A | 8/1998 | Cederholm-Williams |
| 5,795,780 A * | 8/1998 | Cederholm-Williams et al. ............ 435/371 |
| 5,804,428 A | 9/1998 | Edwardson et al. |
| 6,060,461 A * | 5/2000 | Drake ......................... 514/54 |

OTHER PUBLICATIONS

Georgi, M., et al., "Occlusion Of The Renal Artery By Intra-Arterial Injection Of Thrombin In A Case Of Inoperable Renal Tumor", Deutsche Medizinische Wochenschrift, vol. 100(47), pp. 2428–2429, 1975. (Plus English translation).

Lundblad, R.L., et al., "Preparation And Partial Characterization Of Two Forms Of Bovine Thrombin", Biochemical and Biophysical Research Communications, vol. 66(2), pp. 482–489, 1975.

Sakuragawa, N., et al., "Purification And Some Characterization Of Human Thrombin", Acta Medica et Biologica, vol. 23(1), pp. 65–73, 1975.

Fenton, J., et al., "Human Thrombins: Production, Evaluation, And Properties Of α–Thrombin", The Journal of Biological Chemistry, vol. 252(11), pp. 3587–3598, 1977.

Nordenman, B., et al., "Purification Of Thrombin By Affinity Chromatography On Immobilized Heparin", Thrombosis Research, vol. 11, pp. 799–808, 1977.

Nowotny, R., et al., "Mechanical Properties Of Fibrinogen–Adhesive Material", Biomaterials 1980, vol. 3, pp. 677–682, 1982.

Kotelba–Witkowska, B., et al., "Cryopreservation Of Platelet Concentrates Using Glycerol–Glucose", Transfusion, vol. 22(2), pp. 121–124, 1982.

Redl, H., et al., "Fibrin Sealant–Antibiotic Mixture—Stability And Elution Behavior", Fibrinkleber Orthop. Traumatol. Orthop. Symp., vol. 4, pp. 178–181, 1982. (Plus English translation).

Redl, H., et al., "In Vitro Properties Of Mixtures Of Fibrin Seal And Antibiotics", Biomaterials, vol. 4(1), pp. 29–32, 1983.

Gestring, G., et al., "Autologous Fibrinogen For Tissue–Adhesion, Hemostasis And Embolization", Vascular Surgery, vol. 17, pp. 294–304, 1983.

Wolf, G., "The Concentrated Autologous Tissue Glue", Archives of Oto–Rhino–Laryngology, vol. 237, pp. 279–283, 1983.

Tsvetkov, T.S., et al., "A Method For Preparation Of Dry Thrombin For Topical Application", Cryobiology, vol. 21(6), pp. 661–663, 1984.

Yu, X.J., et al., "Affinity Chromatography Of Thrombin On Modified Polystyrene Resins", Journal of Chromatography, vol. 376, pp. 429–435, 1986.

Fischer, A.M., et al., "Thrombin Purification By One–Step Preparative Affinity Chromatography On Modified Polystyrenes", Journal of Chromatography, vol. 363(1), pp. 95–100, 1986.

Harpel, P.C., "Blood Proteolytic Enzyme Inhibitors: Their Role In Modulating Blood Coagulation And Fibrinolytic Enzyme Pathways", pp. 219–234, 1987.

Fenton, J.W., "Regulation Of Thrombin Generation And Functions", Seminars in Thrombosis and Haemostasis, vol. 14(3), pp. 234–240, 1988.

Awano, K., et al., "Role Of Seratonin, Histamine, And Thromboxane A2 In Platelet–Induced Contractions Of Coronary Arteries And Aortae From Rabbits", Journal Of Cardiovascular Pharmacology, vol. 13(5), pp. 781–792, 1989.

Mulvihill, J., et al., "Thrombin Stimulated Platelet Accumulation On Protein Coated Glass Capillaries: Role Of Adhesive Platelet a–Granule Proteins", Thrombosis and Haemostasis, vol. 62(3), pp. 989–995, 1989.

Suzuki, S., et al., "A Study On The Properties Of Commercial Thrombin Preparations", Thrombosis Research, vol. 53(3), pp. 271–277, 1989.

Ronfard, V., et al., "Use of Human Keratinocytes Cultured On Fibrin Glue In The Treatment Of Burn Wounds", Burns, vol. 17(3), pp. 181–184, 1991.

Brennan, M., "Fibrin Glue", Blood Reviews, vol. 5, pp. 240–244, 1991.

DePalma, L., et al., "The Preparation Of Fibrinogen Concentrate For Use As Fibrin Glue By Four Different Methods", Transfusion, vol. 33(9), pp. 717–720, 1993.

McCarthy, P., "Fibrin Glue In Cardiothoracic Surgery", Transfusion Medicine Reviews, vol. 7(3), pp. 173–179, 1993.

Cederholm–Williams, S., "Benefits Of Adjuvant Fibrin Glue In Skin Grafting", The Medical Journal of Australia, vol. 161(9), p. 575, 1994.

Cederholm–Williams, S., "Autologous Fibrin Sealants Are Not Yet Available", The Lancet, vol. 344, p. 336, 1994.

Wiegand, D.A., et al., "Assessment Of Cryoprecipitate–Thrombin Solution for Dural Repair", Head & Neck, pp. 569–573, 1994.

Szczepanski, et al., "Thrombin Clotting Time and Fibrin Polymerization in Liver Cirrhosis", *Materia Medica Polona*, 1994, vol. 26, No. 3, pp. 87–90.

* cited by examiner

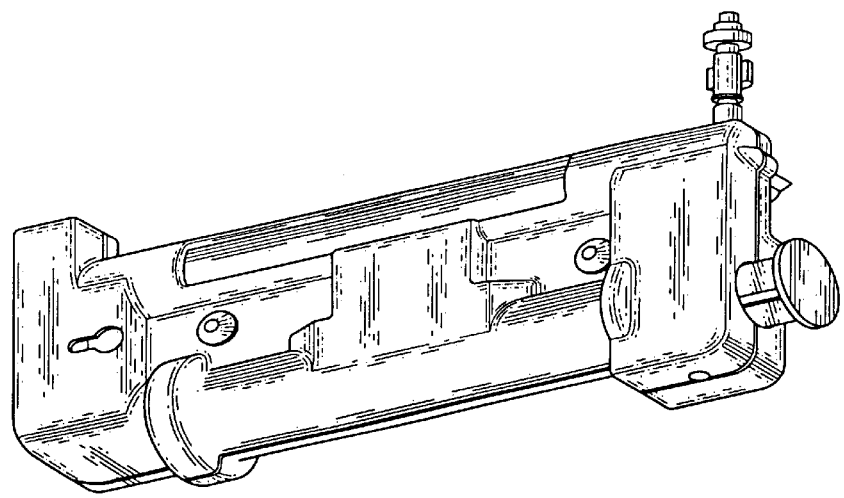
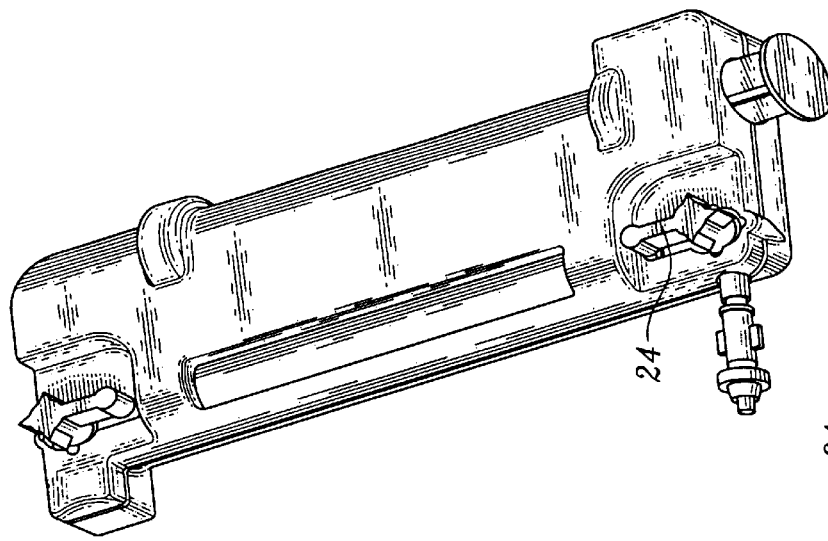
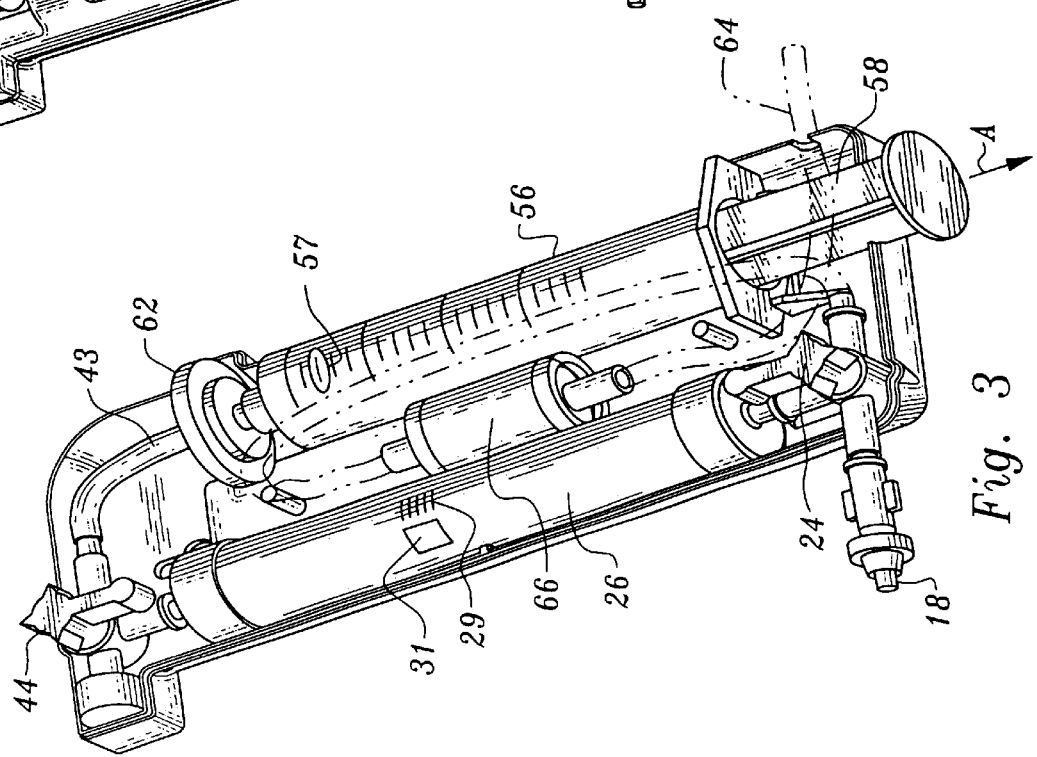

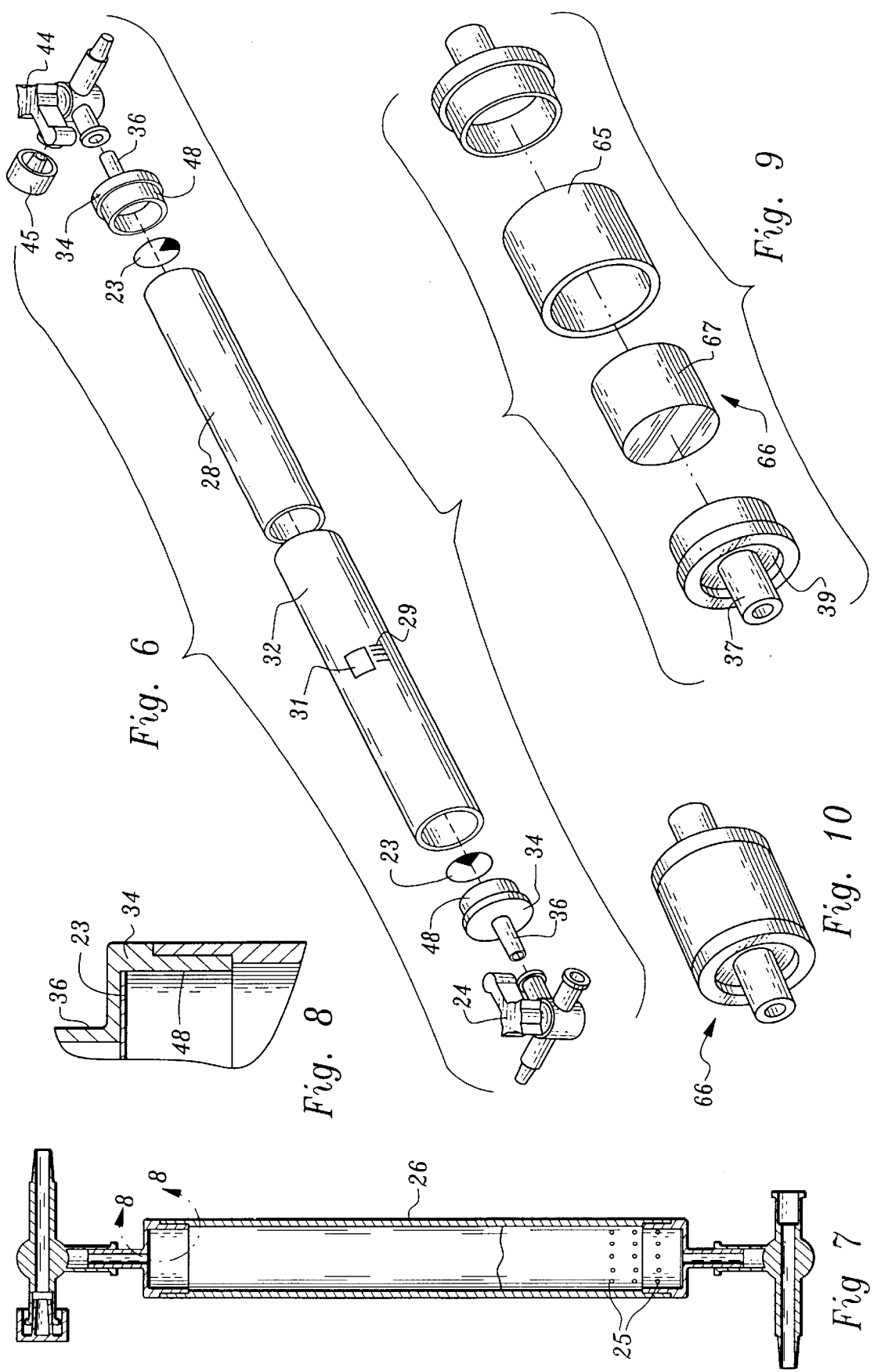

METHOD FOR PREPARING THROMBIN FOR USE IN A BIOLOGICAL GLUE

FIELD OF THE INVENTION

The following invention relates generally to the preparation of a high specific activity thrombin enzyme from a given unit of plasma, which is sufficiently stable that it provides rapid clotting of a fibrinogen-rich solution of clotting and adhesive proteins for more than six hours when held at room temperature or lower.

BACKGROUND OF THE INVENTION

Formulation of a fibrin sealant mimics the last step of the coagulation cascade wherein the enzyme thrombin cleaves fibrinogen which is then cross-linked into a semi-rigid or flexible fibrin clot. This fibrin clot adheres to wound sites, forming a barrier to fluid leaks and generates adhesion between tissues, while providing hemostatic and healing properties to the treated site.

Presently marketed, applicant's CryoSeal™ system is a device which harvests cryoprecipitated, concentrated clotting and adhesive proteins, including fibrinogen and Factor XIII from a donor's plasma in approximately one hour. The one hour cryoprecipitation harvesting, provided by the CryoSeal™ system, compared to the 1 to 2 day cryoprecipitation process routinely practiced in Blood Banks, means that CryoSeal™ harvesting of clotting and adhesive proteins can occur right in the perioperative theater with the patient close by, thereby avoiding the need to initiate the process days in advance.

These CryoSeal™ harvested clotting and adhesive proteins, when combined with bovine or human thrombin, forms a biological glue useful for surgical hemostasis and tissue adhesion. Commercially available thrombin, however, is generally sourced from bovine or human plasma pools, so the patient would still be at risk of negative immune reactions or contamination by infectious blood born viruses and, possibly Crutzfeld-Jacobs Disease (CJD) or new variants of CJD (NVCJD). An advantage of the CryoSeal™ cryoprecipitation invention is that the harvested clotting and adhesive proteins sourced from the patient's own blood eliminates the risk of contamination by infectious blood-borne disease when these clotting and adhesive proteins are topically applied to the patient's surgical wound sites.

It has long been understood, however, that the safest condition for a surgical patient would result from a two component biological sealant preparation in which the thrombin component would be harvested from the same donor in which the clotting and adhesive protein component was harvested—forming a fully autologous biological sealant or glue.

The concept of utilizing thrombin and/or fibrinogen sourced from the patient in a medical procedure performed on that patient is not novel and was first described by Andrianova in 1974. Some twenty years later, Cederholm-Williams PCT Patent (WO94/00566—Jan. 6, 1994) describes an improved fibrin glue in which the thrombin component, which required thirteen steps, including centrifugation, and separation of intermediate precipitates and adjusting the ionic strength of the blood and pH of the plasma to prepare, would be combined with a fibrinogen component also sourced from the plasma of the same donor. However, these many preparation steps are so time consuming they become impractical for use in the perioperative theater where processing times should be less than one hour.

Three years later, in 1997, Hirsh, et al. (U.S. Pat. No. 5,643,192) follows Cederholm-Williams by teaching another method of preparing fibrin glue in which both the fibrinogen and thrombin components of a fibrin glue are sourced from the same donor's plasma. The Hirsh patent describes a method of preparing thrombin in which most of the fibrinogen in the plasma is first precipitated and removed to prepare a supernatant and then clotting the residual fibrinogen in the supernatant which is different and simpler than the method taught by Cederholm-Williams, but does not result in a commercially useful thrombin in that (see FIG. 1 of Hirsh, et al.) the thrombin provides clotting speeds of five seconds or less for only 4 minutes, and less than 10 seconds for only 47 minutes.

These clotting speeds are unsuitable to the needs of surgeons who could not plan their entire surgeries around the limitations of the Hirsh, et al. fibrin glue.

Surgeons predominately require a fast acting clotting time (<5 seconds) for hemostasis and tissue sealing or adhesion. Slow clotting biological glues (>5 seconds) will often be transported away from the wound site by oozing and bleeding before they can perform their function. A surgeon utilizing the Hirsh fibrin glue would be required to arrange his surgery so that the hemostasis and tissue sealing intended for treatment with the Hirsh fibrin glue would occur within the 4 minute window where the clotting time was less than 5 seconds, making the Hirsh invention totally impractical for most surgeries which predominantly require rapid hemostasis and tissue adhesion throughout the surgery, the time span of which could extend to six hours.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

U.S. PATENT DOCUMENTS

| INVENTOR | U.S. PAT. NO. | ISSUE DATE |
| --- | --- | --- |
| Pumphrey | 713,017 | November 4, 1902 |
| Mobley | 1,614,532 | January 18, 1927 |
| Ferry, et al. | 2,533,004 | December 5, 1950 |
| Wahlin | 2,747,936 | May 29, 1956 |
| Clark | 3,179,107 | April 20, 1965 |
| Cobey | 3,223,083 | December 14, 1965 |
| Kennedy, et al. | 3,236,457 | February 22, 1966 |
| Meurer, et al. | 3,269,389 | August 30, 1966 |
| Venus, Jr. | 3,416,737 | December 17, 1968 |
| Horn | 3,467,096 | September 16, 1969 |
| Creighton, et al. | 3,828,980 | August 13, 1974 |
| Green | 3,942,725 | March 9, 1976 |
| Polnauer, deceased, et al. | 3,945,574 | March 23, 1976 |
| Speer | 4,040,420 | August 9, 1977 |
| Reinhardt, et al. | 4,067,333 | January 10, 1978 |
| Kozam, et al. | 4,109,653 | August 29, 1978 |
| Sugitachi, et al. | 4,265,233 | May 5, 1981 |
| Schwarz, et al. | 4,298,598 | November 3, 1981 |
| Redl, et al. | 4,359,049 | November 16, 1982 |
| Schwarz, et al. | 4,362,567 | December 7, 1982 |
| Altshuler | 4,363,319 | December 14, 1982 |
| Schneider | 4,374,830 | February 22, 1983 |
| Schwarz, et al. | 4,377,572 | March 22, 1983 |
| Schwarz, et al. | 4,414,976 | November 15, 1983 |
| Stroetmann | 4,427,650 | January 24, 1984 |
| Stroetmann | 4,427,651 | January 24, 1984 |
| Stroetmann | 4,442,655 | April 17, 1984 |
| Zimmerman, et al. | 4,453,939 | June 12, 1984 |
| Rose, et al. | 4,627,879 | December 9, 1986 |

-continued

| | | |
|---|---|---|
| Redl, et al. | 4,631,055 | December 23, 1986 |
| Sakamoto, et al. | 4,655,211 | April 7, 1987 |
| Silbering, et al. | 4,696,812 | September 29, 1987 |
| Alterbaum | 4,714,457 | December 22, 1987 |
| Koizumi, et al. | 4,734,261 | March 29, 1988 |
| Eibl, et al. | 4,735,616 | April 5, 1988 |
| Saferstein, et al. | 4,752,466 | June 21, 1988 |
| Wolf, et al. | 4,767,416 | August 30, 1988 |
| Skorka, et al. | 4,826,048 | May 2, 1989 |
| Davis | 4,842,581 | June 27, 1989 |
| Miller, et al. | 4,874,368 | October 17, 1989 |
| Avoy | 4,902,281 | February 20, 1990 |
| Seelich | 4,909,251 | March 20, 1990 |
| Tanaka, et al. | 4,923,815 | May 8, 1990 |
| Silbering, et al. | 4,965,203 | October 23, 1990 |
| Capozzi, et al. | 4,978,336 | December 18, 1990 |
| Wolf, et al. | 4,979,942 | December 25, 1990 |
| L'Hermite, et al. | 4,987,336 | January 22, 1991 |
| La Duca | 5,089,415 | February 18, 1992 |
| Kotitschke, et al. | 5,099,003 | March 24, 1992 |
| Wolf, et al. | 5,104,375 | April 14, 1992 |
| Capozzi, et al. | 5,116,315 | May 26, 1992 |
| Nishimaki, et al. | 5,130,244 | July 14, 1992 |
| Kraus, et al. | 5,143,838 | September 1, 1992 |
| Crowley, et al. | 5,151,355 | September 29, 1992 |
| Knighton | 5,165,938 | November 24, 1992 |
| Galanakis | 5,185,001 | February 9, 1993 |
| Morse, et al. | 5,219,328 | June 15, 1993 |
| Fischer | 5,290,259 | March 1, 1994 |
| Sierra, et al. | 5,290,552 | March 1, 1994 |
| Michalski, et al. | 5,304,372 | April 19, 1994 |
| Fischer | 5,328,462 | July 12, 1994 |
| Lonneman, et al. | 5,368,563 | November 29, 1994 |
| Linnau | 5,393,666 | February 28, 1995 |
| Epstein | 5,405,607 | April 11, 1995 |
| Marx | 5,411,885 | May 2, 1995 |
| Kikuchi, et al. | 5,443,959 | August 22, 1995 |
| Miller, et al. | 5,474,540 | December 12, 1995 |
| Broly, et al. | 5,474,770 | December 12, 1995 |
| Weis-Fogh, et al. | 5,480,378 | January 2, 1996 |
| Proba, et al. | 5,506,127 | April 9, 1996 |
| Cochrum | 5,510,102 | April 23, 1996 |
| Antanavich, et al. | 5,585,007 | December 17, 1996 |
| Pines, et al. | 5,605,887 | February 25, 1997 |
| Cochrum | 5,614,204 | March 25, 1997 |
| Marx | 5,631,019 | May 20, 1997 |
| Hirsh, et al. | 5,643,192 | July 1, 1997 |
| Epstein | 5,648,265 | July 15, 1997 |
| Edwardson, et al. | 5,750,657 | May 12, 1998 |
| Cederholm-Williams | 5,795,571 | August 18, 1998 |
| Cederholm-Williams | 5,795,780 | August 18, 1998 |
| Edwardson, et al. | 5,804,428 | September 8, 1998 |

FOREIGN PATENT DOCUMENTS

| APPLICANT | COUNTRY | PATENT NO. | ISSUE DATE |
|---|---|---|---|
| Zdaril | DE | DE 25,913 | February 12, 1884 |
| Szent-Györgyi, et al. | CH | 259,254 | June 1, 1949 |
| The Trustees of Columbia University in the City of New York | WIPO | WO 86/01814 | March 27, 1986 |
| Weis-Fogh | WIPO | WO 88/02259 | April 7, 1988 |
| Board of Regents, The University of Texas System | WIPO | WO 88/03151 | May 5, 1988 |
| | SU | 1,527,261 A1 | December 7, 1989 |
| Cryolife, Inc. | WIPO | WO 91/09641 | July 11, 1991 |
| Baxter International, Inc. | EP | 0 443 724 A1 | August 28, 1991 |
| Warner-Lambert Co. | EP | 0 505 604 A1 | September 30, 1992 |
| Octapharma AG | EP | 0 534 178 A2 | March 31, 1993 |
| Cryolife, Inc. | WIPO | WO 93/19805 | October 14, 1993 |
| Cederholm-Williams, et al. | WIPO | WO 94/00566 | January 6, 1994 |
| E. R. Squibb & Sons | EP | 0 592 242 A1 | April 13, 1994 |
| Plasmaseal Corporation | WIPO | WO 96/17871 | June 13, 1996 |

OTHER PRIOR ART (INCLUDING AUTHOR, TITLE, PERTINENT PAGES, DATE, ETC.)

Fenton, J. W., et al., "Human Thrombins", Chemistry & Biology of Thrombin, pp. 43–70.

Rosenberg, R. D., et al., "Bovine Thrombin: Constant Specific Activity Products From Single Animals", Fed. Proc., p. 321, Abstract No. 361.

Quick, A. J., et al., "Production Of Thrombin From Precipitate Obtained By Acidification Of Diluted Plasma", pp. 114–118.

Eagle, H., "Studies On Blood Coagulation", pp. 531–545, 1934.

Mann, K. G., et al., "The Molecular Weights Of Bovine Thrombin And Its Primary Autolysis Products", pp. 6555–6557, 1969.

Mann, K. G., et al., "Multiple Active Forms Of Thrombin", pp. 5994–6001, 1971.

Martin, M., et al., "Thrombolysis In Patients With Chronic Arterial Occlusions", Thrombolytic Therapy, Vol. 47, pp. 235–241, 1971.

Fenton, J. W., et al., "Large-Scale Preparation And Preliminary Characterizations Of Human Thrombin", Biochimica et Biophysica Acta. Vol. 229, pp. 26–32, 1971.

Andrianova, et al., "An Accessible Method Of Simultaneous Production Of Fibrinogen And Thrombin From Blood", pp. 648–650, 1975. (Plus English translation).

Georgi, M., et al., "Occlusion Of The Renal Artery By Intra-Arterial Injection Of Thrombin In A Case Of Inoperable Renal Tumor", Deutsche Medizinische Wochenschrift, Vol. 100(47), pp. 2428–2429, 1975. (Plus English translation).

Lundblad, R. L., et al., "Preparation And Partial Characterization Of Two Forms Of Bovine Thrombin", Biochemical and Biophysical Research Communications, Vol. 66(2), pp. 482–489, 1975.

Sakuragawa, N., et al., "Purification And Some Characterization Of Human Thrombin", Acta Medica et Biologica, Vol. 23(1), pp. 65–73, 1975.

Fenton, J. W., et al., "Human Thrombins: Production, Evaluation, And Properties Of α-Thrombin", The Journal of Biological Chemistry, Vol. 252(11), pp. 3587–3598, 1977.

Nordenman, B., et al., "Purification Of Thrombin By Affinity Chromatography On Immobilized Heparin", Thrombosis Research, Vol. 11, pp. 799–808, 1977.

Nowotny, R., et al., "Mechanical Properties Of Fibrinogen-Adhesive Material", Biomaterials 1980, Vol. 3, pp. 677–682, 1982.

Kotelba-Witkowska, B., et al., "Cryopreservation Of Platelet Concentrates Using Glycerol-Glucose", Transfusion, Vol. 22(2), pp. 121–124, 1982.

Redl, H., et al., "Fibrin Sealant-Antibiotic Mixture—Stability And Elution Behavior", Fibrinkleber Orthop. Traumatol. Orthop. Symp., Vol. 4, pp. 178–181, 1982. (Plus English translation).

Redl, H., et al., "In Vitro Properties Of Mixtures Of Fibrin Seal And Antibiotics", Biomaterials, Vol. 4(1), pp. 29–32, 1983.

Gestring, G., et al., "Autologous Fibrinogen For Tissue-Adhesion, Hemostasis And Embolization", Vascular Surgery, Vol. 17, pp. 294–304, 1983.

Wolf, G., "The Concentrated Autologous Tissue Glue", Archives of Oto-Rhino-Laryngology, Vol. 237, pp. 279–283, 1983.

Tsvetkov, T. S., et al., "A Method For Preparation Of Dry Thrombin For Topical Application", Cryobiology, Vol. 21(6), pp. 661–663, 1984.

Yu, X. J., et al., "Affinity Chromatography Of Thrombin On Modified Polystyrene Resins", Journal of Chromatography, Vol. 376, pp. 429–435, 1986.

Fischer, A. M., et al., "Thrombin Purification By One-Step Preparative Affinity Chromatography On Modified Polystyrenes", Journal of Chromatography, Vol. 363(1), pp. 95–100, 1986.

Harpel, P. C., "Blood Proteolytic Enzyme Inhibitors: Their Role In Modulating Blood Coagulation And Fibrinolytic Enzyme Pathways", pp. 219–234, 1987.

Fenton, J. W., "Regulation Of Thrombin Generation And Functions", Seminars in Thrombosis and Hemostasis, Vol. 14(3), pp. 234–240, 1988.

Awano, K., et al., "Role Of Seratonin, Histamine, And Thromboxane $A_2$ In Platelet-Induced Contractions Of Coronary Arteries And Aortae From Rabbits", Journal Of Cardiovascular Pharmacology, Vol. 13(5), pp. 781–792, 1989.

Mulvihill, J., et al., "Thrombin Stimulated Platelet Accumulation On Protein Coated Glass Capillaries: Role Of Adhesive Platelet α-Granule Proteins", Thrombosis and Haemostasis, Vol. 62(3), pp. 989–995, 1989.

Suzuki, S., et al., "A Study On The Properties Of Commercial Thrombin Preparations", Thrombosis Research, Vol. 53(3), pp. 271–277, 1989.

Ronfard, V., et al., "Use of Human Keratinocytes Cultured On Fibrin Glue In The Treatment Of Burn Wounds", Burns, Vol. 17(3), pp. 181–184, 1991.

Brennan, M., "Fibrin Glue", Blood Reviews, Vol. 5, pp. 240–244, 1991.

DePalma, L., et.al., "The Preparation Of Fibrinogen Concentrate For Use As Fibrin Glue By Four Different Methods", Transfusion, Vol. 33(9), pp. 717–720, 1993.

McCarthy, P., "Fibrin Glue In Cardiothoracic Surgery", Transfusion Medicine Reviews, Vol. 7(3), pp. 173–179, 1993.

Cederholm-Williams, S., "Benefits Of Adjuvant Fibrin Glue In Skin Grafting", The Medical Journal of Australia, Vol. 161(9), p. 575, 1994.

Cederholm-Williams, S., "Autologous Fibrin Sealants Are Not Yet Available", The Lancet, Vol. 344, p. 336, 1994.

Wiegand, D. A., et al., "Assessment Of Cryoprecipitate-Thrombin Solution for Dural Repair", Head & Neck, pp. 569–573, 1994.

The other prior art listed above, not all of which are specifically discussed catalog the prior art of which the applicant is aware. These undiscussed references diverge even more starkly from the instant invention specifically distinguished below.

SUMMARY OF THE INVENTION

The instant invention addresses the long felt need for a simple, practical, fast method of preparing stable human thrombin from a donor's blood, which will provide fast clots (<5 seconds) throughout a lengthy surgery (e.g. six hours) to combine with the clotting and adhesive proteins harvested and concentrated from the same unit of blood to form a biological sealant with no patient exposure to microbial or possible CJD or NVCJD contaminations. Previous works in the field (Hirsch, et al.) exemplified a thrombin with minimal stability in that the thrombin achieved rapid clotting of fibrinogen (i.e., less than 5 seconds) during only a very narrow four to five minute time period, or required so many steps and elapsed time it would not be suitable for perioperative preparation, both totally impractical for the broad range of surgeries.

The present invention provides a stable thrombin enzyme which can cause precise, repeatable fast or slow polymerization of clotting and adhesive proteins over a duration of up to six hours—throughout even a long surgery. Further, the use of clotting and adhesive proteins and thrombin all sourced from a single donor will eliminate various disease risks posed from the use of commercial fibrin glues where the fibrinogen is sourced from plasma pooled from thousands of donors and the thrombin is either sourced from a similar pool of human plasma or of bovine origin. The speed and simplicity of the production of stable thrombin by use of this invention allows it to be prepared just prior to or during operative procedures and it will provide fast clotting throughout even the longest surgeries. The thrombin produced by this invention can be diluted in saline, water and a dilute $CaCl_2$ solution (e.g. 125 mM $CaCl_2$) to provide precise, slower clotting times thereby allowing any preferred time from less than five seconds to longer than 2 minutes.

The procedure of the invention is preferably comprised of three steps, the first two of which should preferably occur at the same time:

1. Preparing a fraction enriched in prothrombin by use of Ethanol to substantially enhance the concentration of prothrombin and at the same time remove or denature naturally occurring ingredients within plasma, such as Fibrinogen and Antithrombin III which can bind to, block, interfere with or inhibit prothrombin or its subsequent activation to long-term functional thrombin.

2. Adding calcium ions to the enriched prothrombin solution and briefly agitating the solution to convert the pro-thrombin to stable, long term thrombin.

3. Expressing the thrombin solution through a filter to remove particulate matter which would prevent spraying the thrombin through a small orifice or expressing the thrombin through a thin tube onto a wound site.

OBJECTS OF THE INVENTION

Accordingly, it is a primary object of the present invention to provide a new and novel apparatus and method to derive fast acting, stable autologous thrombin from the donor's plasma.

It is a further object of the present invention to provide thrombin as characterized above which has a shelf life longer than most associated surgical procedures.

It is a further object of the present invention to provide thrombin as characterized above in which the clotting time can be predictably lengthened at will through dilution with saline.

It is a further object of the present invention to provide thrombin as characterized above which has simple preparatory procedures.

It is a further object of the present invention to provide a method for producing thrombin as characterized above which has a process time in as little as thirty minutes, up to seventy-five minutes.

It is a further object of the present invention to provide thrombin which can be sprayed through small orifices or expressed through thin tubes.

Viewed from a first vantage point it is the object of the present invention to provide a novel and practical method for producing stable human thrombin from a prothrombin fraction which has been substantially enriched by ethanol fractionation to increase the prothrombin concentration and at the same time remove contaminating proteins. The addition of calcium chloride to the enriched prothrombin converts prothrombin to thrombin. From the same sole donor plasma, clotting and adhesive proteins are simultaneously obtained by other means to comprise the second component necessary for the autologous biological sealant.

Viewed from a second vantage point, it is an object of the present invention to provide a method for generating autologous thrombin from a patient, the steps including: obtaining a blood product from the patient; sequestering plasma from the product; enriching the prothrombin in a plasma fraction; converting the prothrombin to thrombin, and filtering particulate from the thrombin.

Viewed from a third vantage point, it is an object of the present invention to provide a method for producing autologous thrombin which is stable for more than fifteen minutes, the steps including: sequestering pro-thrombin from plasma and converting the pro-thrombin to thrombin.

Viewed from a fourth vantage point, it is an object of the present invention to provide an autologous thrombin which provides fast clotting in less than five seconds for more than fifteen minutes.

Viewed from a fifth vantage point, it is an object of the present invention to provide a composition for extracting thrombin from plasma consisting essentially of: Plasma; Ethanol (ETOH); $CaCl_2$.

Viewed from a sixth vantage point, it is an object of the present invention to provide a method for preparing thrombin comprising: obtaining plasma; adding ETOH and $CaCl_2$ to the plasma, forming a composition: agitating the composition; incubating the composition in a static or rocking mode; filtering the composition of particulate, thereby passing the thrombin through the filter.

Viewed from a seventh vantage point, it is an object of the present invention to provide a device for preparing thrombin from plasma, comprising: a reaction chamber having a solution of $CaCl_2$ and ETOH therein; means for admitting plasma into the reaction chamber; thrombin receiving syringe coupled to the reaction chamber to receive the thrombin; and a filter located between the reaction chamber and the thrombin receiving syringe.

Viewed from an eighth vantage point, it is an object of the present invention to provide an autologous biological glue processing device, comprising, in combination: a thrombin processing means, a clotting and adhesive proteins processing means operatively coupled to the thrombin processing means, means for receiving plasma via the operative coupling for subsequent conversion of the plasma to, respectively thrombin and clotting and adhesive proteins.

The present invention provides a method and apparatus that produces thrombin which is sufficiently stable that it can provide less-than-5-second clots for up to six hours, substantially more stable than demonstrated in all prior art. Further, the clot time can be modified at will through dilution with saline.

The present invention further provides an efficient method of preparation. Improved cryoprecipitation of clotting and adhesive proteins through the CryoSeal™ invention requires less than one hour. In this same time frame, the autologous human thrombin component can be manufactured with minimal materials and methods from the same source plasma. Both of the biological components of the biological glue are easily combined in a surgical setting, administered to the very same donor patient, and the resultant clotting provides hemostasis or tissue adhesion at the wound site.

The present invention additionally provides a method for sterile production of both components of the biological glue. The improved sterile manufacturing described herein provides a final product that is essentially free of contamination by non autologous microbes.

These and other objects will be made manifest when considering the following detailed specification when taken in conjunction with the appended drawing figures.

BRIEF DESCRIPTION OF THE DRAWINGS

FIG. 3 is a perspective view of the interior of the thrombin processing case with the thrombin syringe shown in FIG. 2 removed therefrom.

FIG. 4 is a perspective view of the thrombin case upper half.

FIG. 5 is a perspective view of the thrombin case lower half.

FIG. 6 is an exploded parts view of the reaction chamber 26 shown in FIG. 3 along with the valving structure at opposed ends thereof.

FIG. 7 is a sectional view of the reaction chamber and valving structure depicted in FIG. 6.

FIG. 8 is a detail of construction of one component of that which is shown in FIG. 7.

FIG. 9 is an exploded parts view of a filter shown in FIG. 3.

FIG. 10 is a perspective view of that which is shown in FIG. 9.

DESCRIPTION OF PREFERRED EMBODIMENTS

Figure 1:
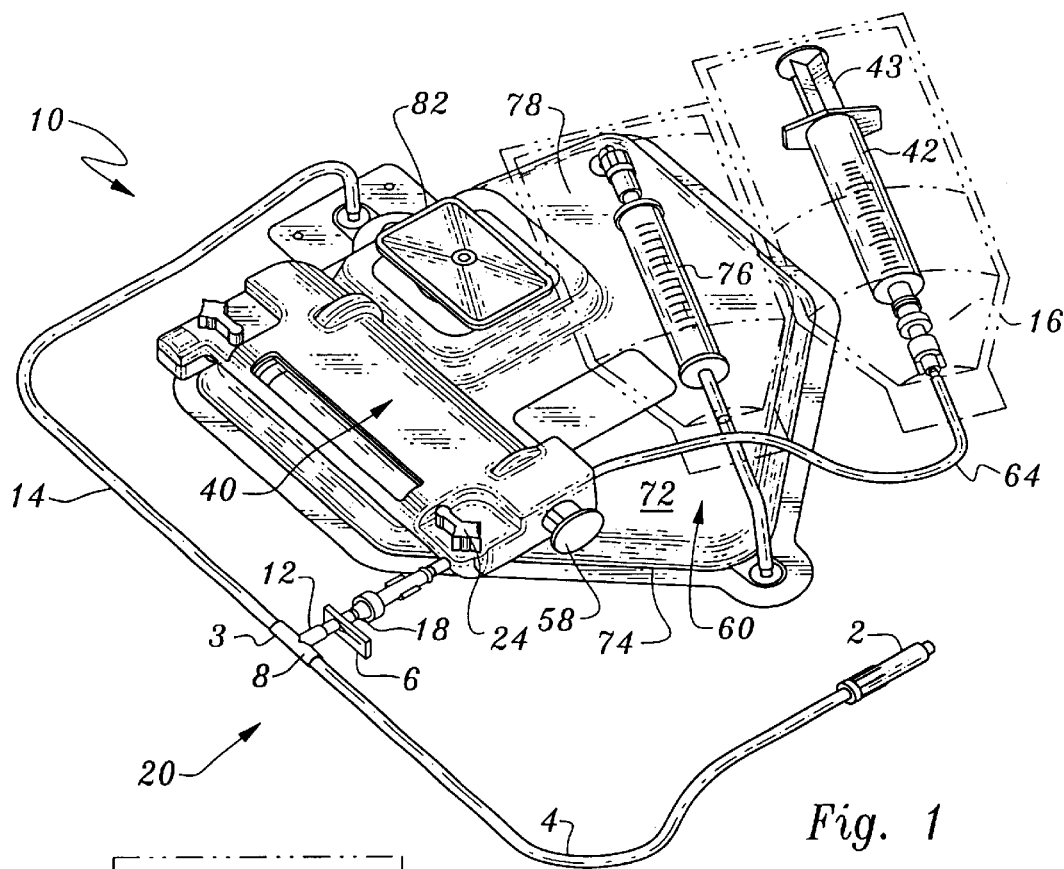
FIG. 1 is a perspective view of an apparatus for sequestering prothrombin from plasma, processing the prothrombin into thrombin and taking the plasma not relegated towards the prothrombin and extracting clotting and adhesive proteins therefrom.

Referring to the drawings, wherein like elements denote like parts throughout, reference numeral 10 is directed to the processing set according to the present invention and shown in FIG. 1.

In its essence, the processing set 10 includes a fluid receiving system 20 which communicates with both a thrombin processing unit 40 and a clotting and adhesive proteins processing unit 60.

More particularly, the fluid receiving system 20 includes an inlet 2 communicating with tubing 4 through which plasma will enter the processing units 40, 60. The conduit 4 has plural stop valves 6 which can occlude the tubing 4 preventing fluids through passage. The tubing 4 communicates through a T fitting 8 to divide plasma into two branches, a first branch 12 which leads to the thrombin processing unit 40 and a second branch 14 leading to the clotting and adhesive proteins processing unit 60. The first valve branch 12 also includes a stop valve 6.

Since it is preferred that the blood product admitted to the inlet 2 be plasma, the whole blood is first processed either by filtering, centrifugation, or another means of settling to remove the heavier red blood cells from the blood products, leaving plasma therebeyond for use in the FIG. 1 device. Although this system can be dimensioned for any size batch, the plasma required for the thrombin processing unit will typically be 9–10 ml. so that the final volume of concentrated thrombin matches a typical yield of cryoprecipitated clotting and adhesive proteins from the clotting and adhesive proteins processing unit 60. A sealed bag 16 overlies the thrombin dispensing syringe 42 (and a lead in of conduit 64) to provide sterility until the thrombin dispensing syringe 42 is introduced into a sterile surgical field (e.g., operatory).

Figure 2:
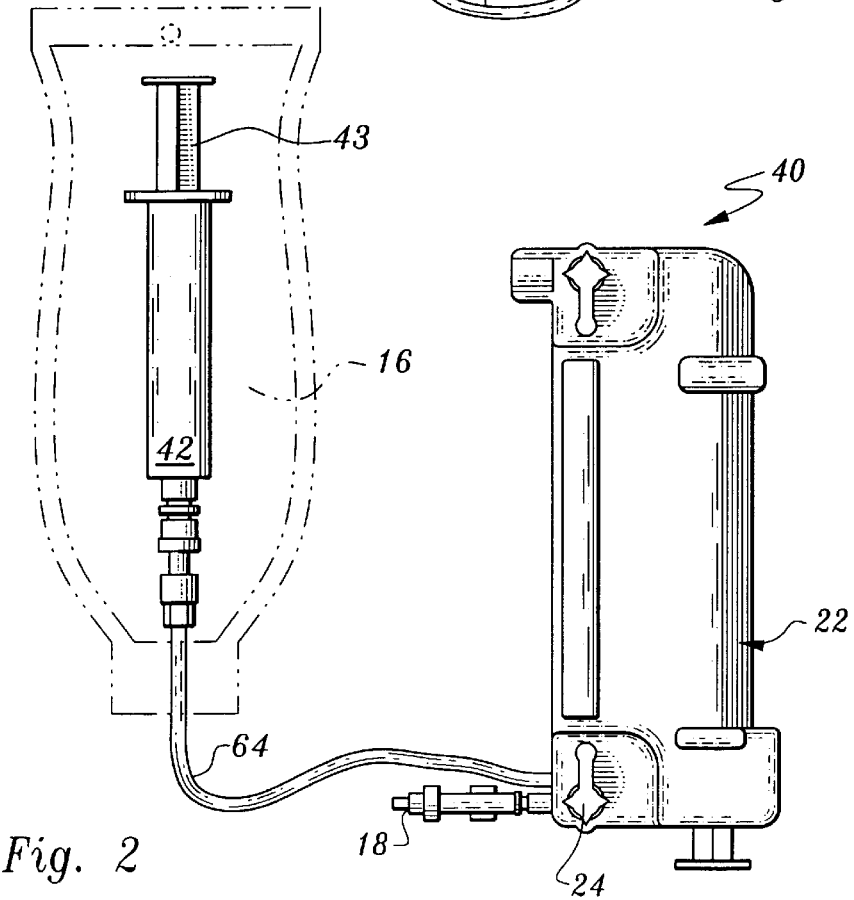
FIG. 2 is a plan view of the thrombin processing set removed from the processing set that extracts clotting and adhesive proteins.

Prior to that, the thrombin processing unit 40 operates as shown and described with reference to FIGS. 2 through 10. As mentioned, fluid enters the first branch 12 and (FIG. 1) passes beyond a coupling 18 and into an interior of a casing 22. Coupling 18 is preferably frictionally and/or adhesively attached to the first branch 12 yet the thrombin processing unit 40 can still be removed (e.g. FIG. 2) from the processing set 10 (e.g., by merely detaching or severing branch 12 followed perhaps with heat sealing) after receiving the plasma as shown in FIG. 2. If adhesive is used, it is a sterile grade for use in an operatory.

Referring to FIG. 3, a valve 24 initially directs the plasma to a reaction chamber 26 having an interior tube 28 (FIG. 6) preferably formed from glass and capable of receiving a volume, for example 15 ml. Glass tube 28 is preferably shorter than and circumscribed by an overlying barrel 32 preferably formed from PVC. A window 31 in the PVC barrel 32 can be used to gauge and/or verify the contents within the glass tube 28. Gauging may also include gradations 29, indicating a volume on the glass tube. The glass tube 28 of the reaction chamber 26 receives the plasma from the first branch 12 and into its interior for mixing with reagents preloaded in the glass tube 28 and described hereinafter. As shown in FIG. 7, the interior of the glass tube is preferably prefilled only partially with beads 25 preferably formed from borosilicate to enhance the reaction and agitation.

The reaction chamber 26 is formed with first and second end caps 34 detailed in FIGS. 6 through 8. Each end cap includes a central outwardly conically tapering spout 36 which communicates with the valve 24 at one end and a further valve 44 at an opposite end. Each spout 36 is isolated from the beads 25 by a screen 23 nested within necked-down portion 48. Valve 24 has three branches as does valve 44, but valve 44 has one branch capped off with a cap 45 thereby defining a two branch valve. One branch of each valve 24, 44 communicates with a respective one spout 36 projecting out from each cap 34. Fluid communication exists between one branch of each valve and its spout into the interior of the glass tube 28 and through flow is controlled by the valves 24, 44. As shown in FIG. 8, the cap 34 includes an annular necked-down portion 48 which frictionally and/or adhesively resides within an interior hollow of the PVC barrel 32. In this way, the necked-down portion 48 rests upon ends of the glass tube 28 in sealing engagement therewith, isolating the interior of the reaction chamber from the PVC barrel 32.

Preferably, ethanol and calcium chloride are the reagents which have been preloaded into the reaction chamber 26. Initially, both valves 24 and 44 are oriented so that reagents will not pass therebeyond to seal the chamber. After the plasma has been pumped into processing unit 60, valve 44 is turned to allow access to the draw plunger 56 and valve 24 is oriented to allow access between the passageway 21 and the reaction chamber 26. Slide clip 6 is opened with the thrombin processing unit 40 held vertically with respect to the plan shown in FIG. 1, syringe 56 plunger 58 is moved along the direction of the arrow A to evacuate air from chamber 26. More specifically, the path 43 between valve 44 and syringe 56 includes a filter 62 located in the flow path. The filter 62 provides an aeseptic microbial barrier so that, upon subsequent delivery of the thrombin to the dispensing syringe 42 (FIG. 1), there is no contamination from around the seal 57 of plunger 58 delivered to syringe 42. Plasma will subsequently enter chamber 26 from conduit 4 to replace air. Valve 24 is oriented to address filter 66. The reagents and plasma are briefly agitated assisted by beads 25 (and allowed to incubate for about 60 minutes). After incubation, thrombin processing unit 40 is agitated to loosen and break up gel formation. The plunger of syringe 56 is pushed in the direction opposite arrow A to move thrombin from chamber 26 through filter 66 into syringe 42. Delivery of thrombin to syringe 42 can be enhanced by retracting plunger 43 of syringe 42, defining a push pull system. Filter 66 removes particulate matter from the thrombin, including gel.

FIGS. 9 and 10 reveal the filter 66 includes an outer cylindrical wall 65 with end caps 34 each having a cylindrical spout 37 circumscribed by an annular recess 39. The centrally disposed cylindrical filter element 67 is preferably formed from polyurethane foam. Filter 67 filters by weight, size and protein binding.

Allowing the thrombin contained in the reaction chamber 26 to reside therein after agitation for 30 to 75 (until a gel formation occurs in the reaction chamber) enhances the effectiveness of the filter 66 in removing particulate matter for subsequent utilization. The time span for conversion and activation allows enough particulate matter to be removed by the filter to optimize the use of the thrombin later in a narrow orificed dispenser, such as a sprayer, or expression through a thin tube.

Referring back to FIG. 1, attention is now directed to the clotting and adhesive protein processing unit 60. All of the plasma not diverted to the thrombin processing unit 40 is admitted to an interior chamber 72 of the clotting and adhesive protein processing unit 60. The clotting and adhesive protein processing unit 60 is manipulated by heat exchange and rotation so that all clotting and adhesive proteins extracted from the plasma will sediment at a nose 74 of the chamber 72 for subsequent extraction by means of a clotting and adhesive protein dispensing syringe 76 contained in a sterile pouch 78. Chamber 72 is protected during this process by a filter vent 82 preventing contamination. Once the thrombin has been loaded into the dispensing syringe 42, and the clotting and adhesive proteins have been loaded into the clotting and adhesive dispensing syringe 76, the two syringes can be decoupled from the processing set 10 (e.g. sterile disconnect device), passed into the sterile, surgical arena where the contents are dispensed into sterile 3 cc plastic syringes which are subsequently loaded into the fibrin glue applicator for spraying or line and dot application. Mixing the thrombin with the clotting and adhesive proteins forms the biological glue.

Both dispensing syringes 42 and 76 are stored at room temperature, or preferably at 2 C. to 8 C. prior to usage. Please see FIGS. 13 through 16.

Figure 11:
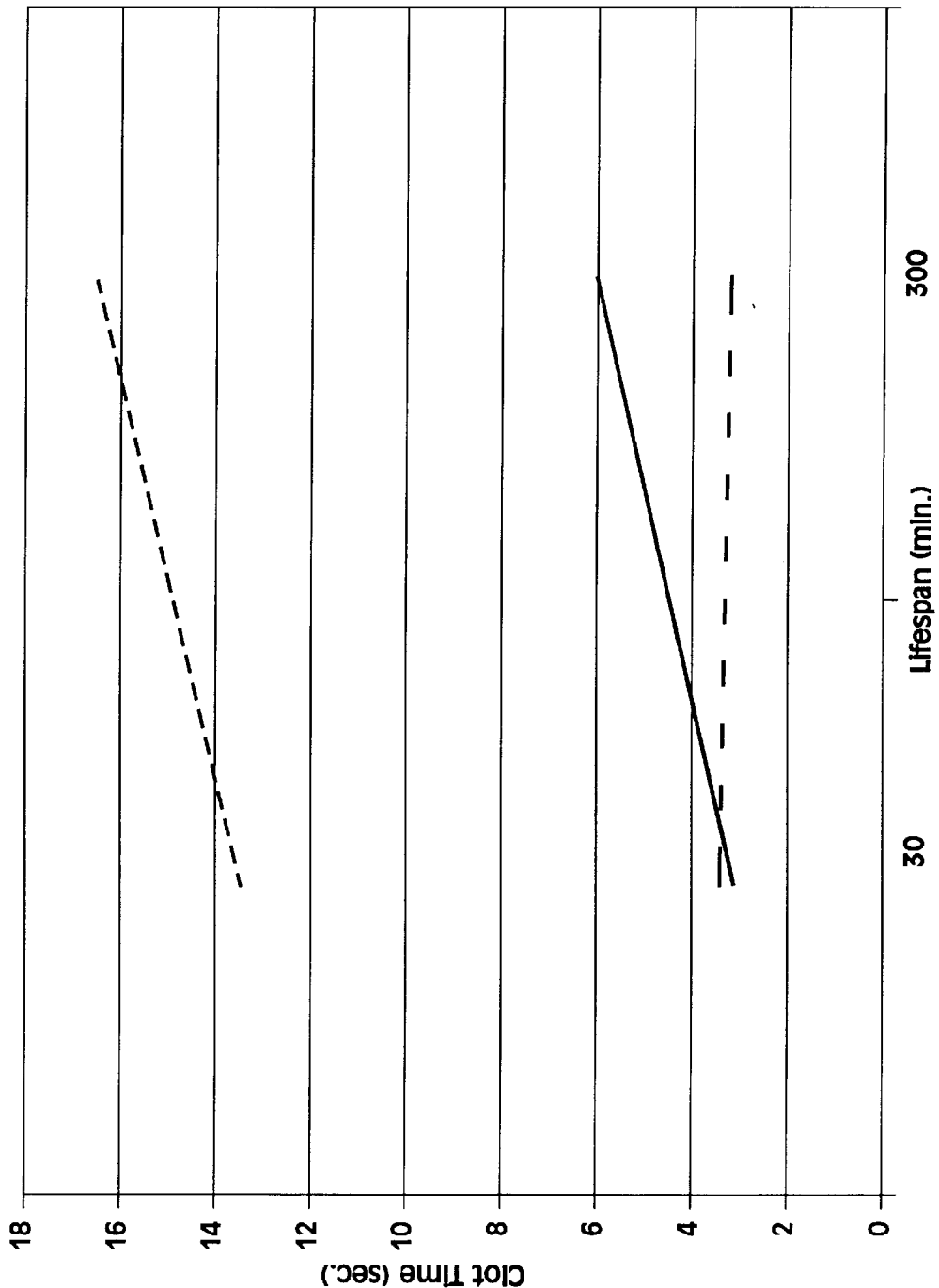
FIG. 11 graphs clot time versus lifespan of thrombin fractionated at different ETOH concentrations.

Assume 9–10 ml of room temperature plasma is introduced into the reaction chamber 26. Add 1.0 ml of 75 mM calcium chloride ($CaCl_2$) and 2.0 ml of ethanol (ETOH) (i.e., ethanol taken from a 100% "stock" bottle and added to comprise 18.9% volume/unit volume or 15.02% ethanol weight/unit volume). The thrombin life A span is shown to have been at least 300 minutes while its clotting time is at 2.98 seconds. An ethanol final concentration range between 8.0% and 20.0% (volume/unit volume), however, still has utility. Please see FIG. 11.

Figure 12:
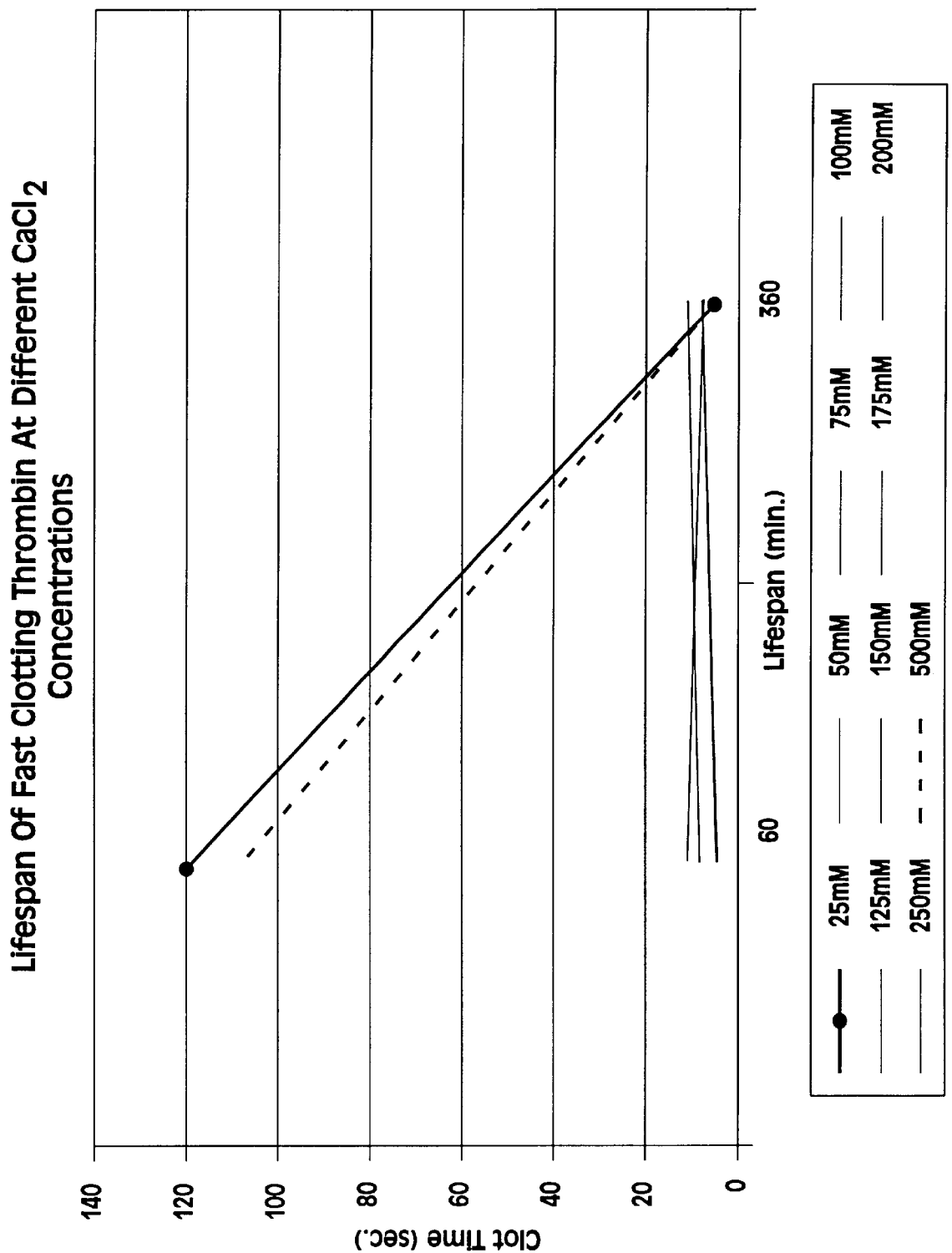
FIG. 12 graphs clot time versus lifespan of thrombin fractionated at different ETOH concentrations at different $CaCl_2$ concentrations.
Figure 13:
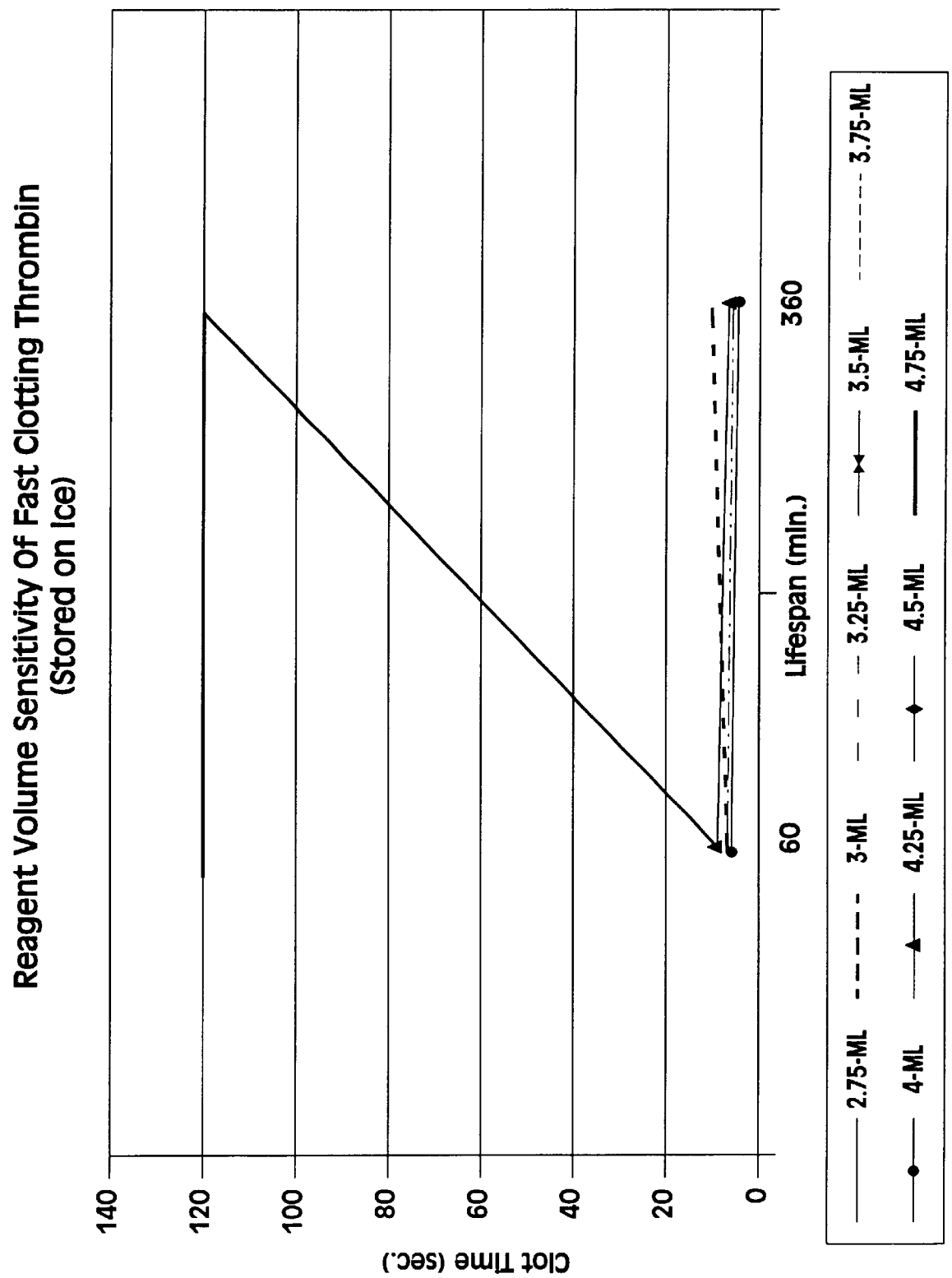
FIG. 13 graphs clot time versus lifespan of thrombin showing reagent volume sensitivity when the thrombin is stored on ice.
Figure 14:
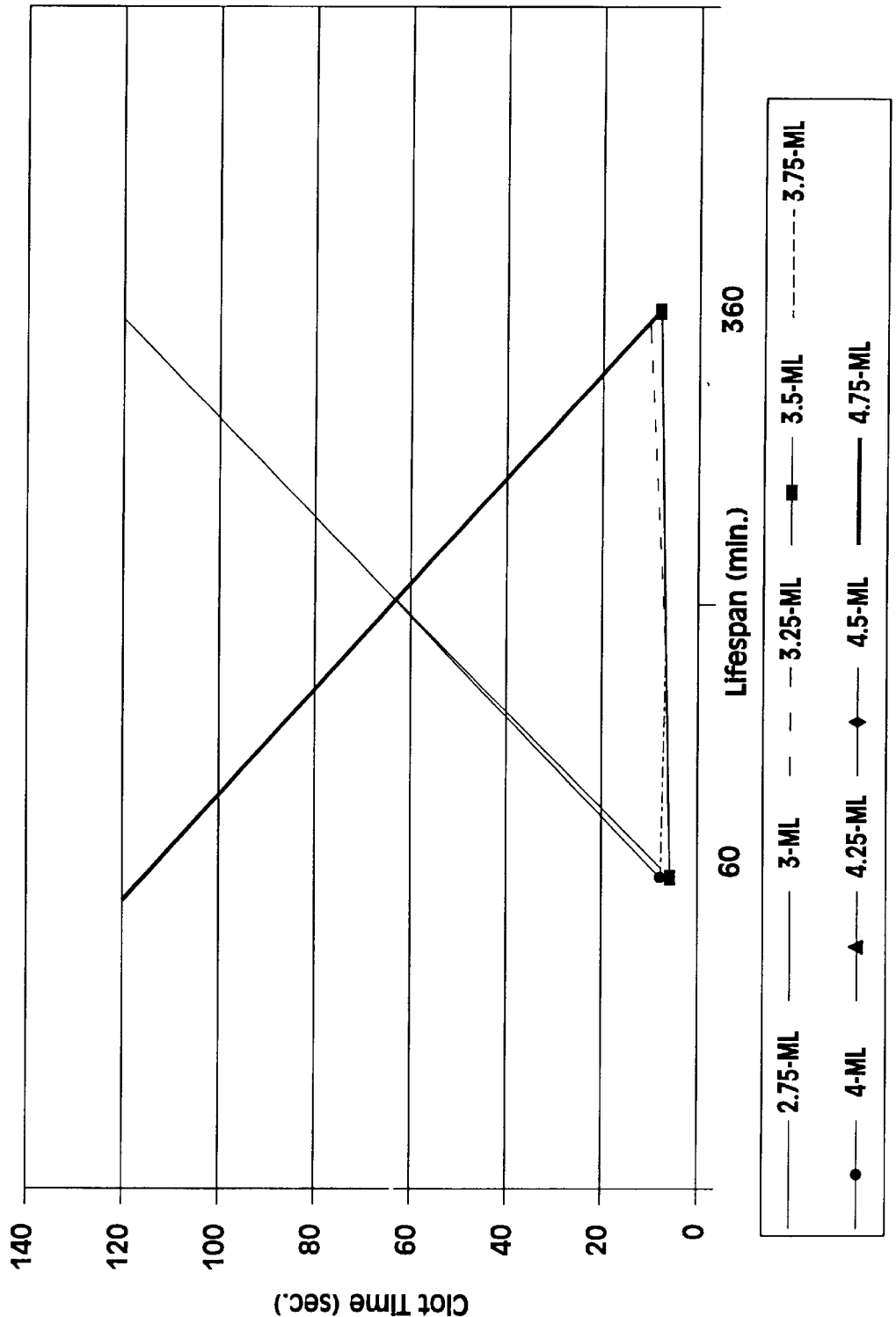
FIG. 14 graphs clot time versus lifespan of thrombin showing reagent volume sensitivity when the thrombin is stored at room temperature.
Figure 15:
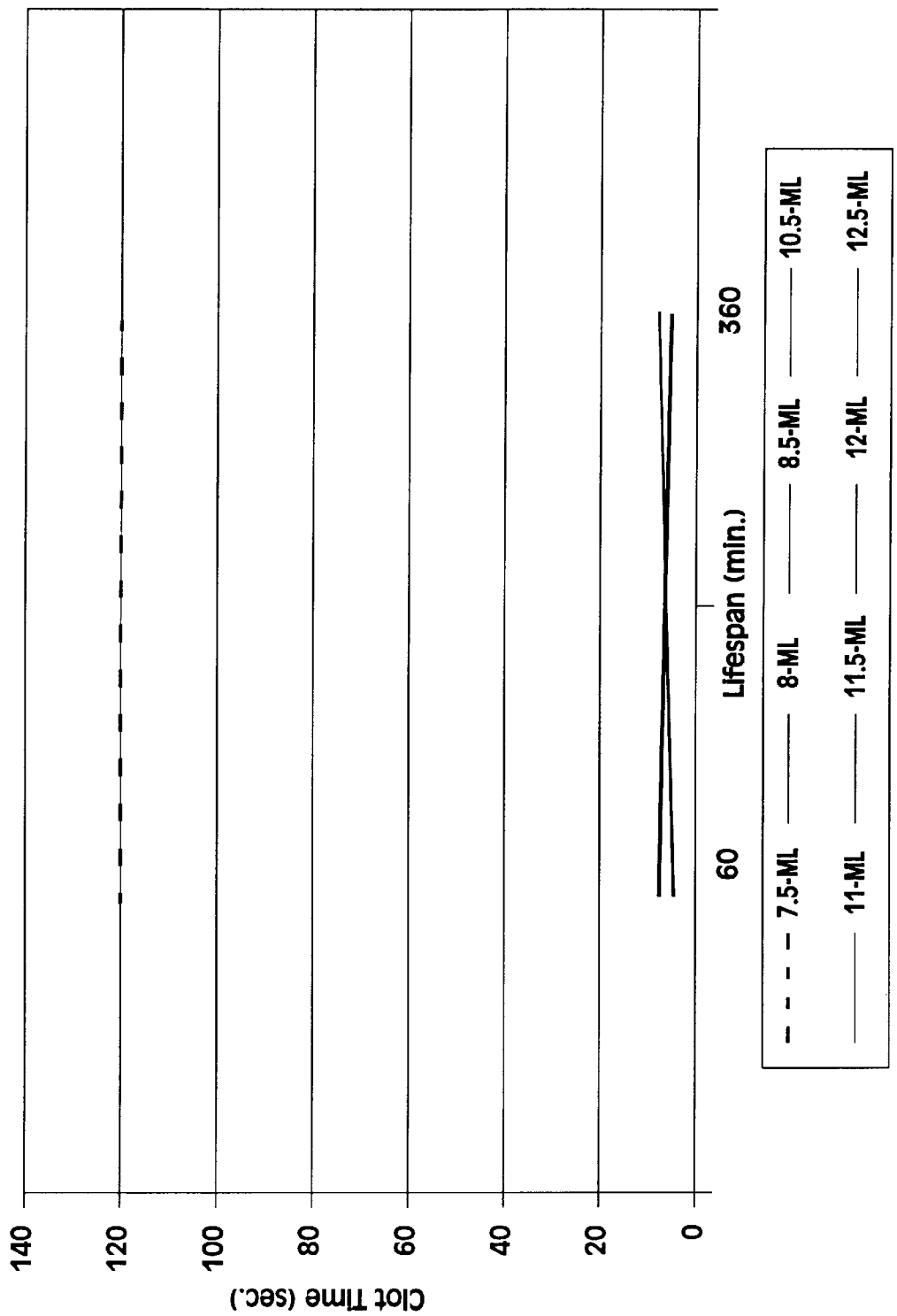
FIG. 15 graphs clot time versus lifespan of thrombin showing plasma volume sensitivity when the thrombin is stored on ice.
Figure 16:
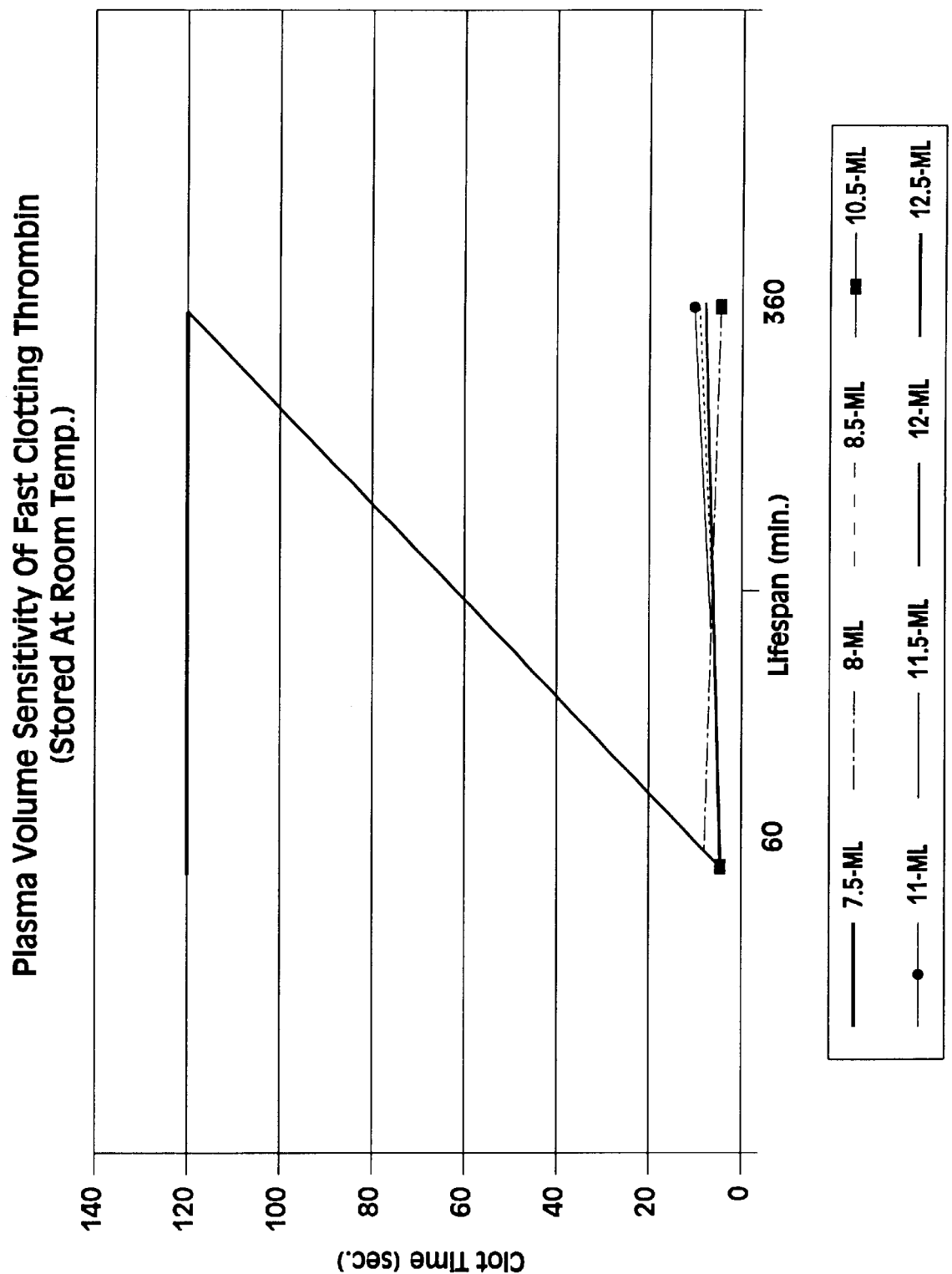
FIG. 16 graphs clot time versus lifespan of thrombin showing plasma volume sensitivity when the thrombin is stored at room temperature.

When the ethanol is at a final concentration of 18.9% volume/unit volume (as above) and the calcium chloride final concentration is 5.7 mM (1 ml taken from a 75 mM stock solution of calcium chloride), the thrombin lifespan also extends to at least 360 minutes while maintaining a clot time of 5.98 seconds. Calcium chloride final concentrations ranging between 4.5 mM and 23.0 mM, however, have utility. Please see FIG. 12.

Solutions such as saline, dilute $CaCl_2$ (e.g. 125 mM $CaCl_2$) or even water added to the thrombin can alter both the clotting time and life span of the thrombin. Assume an ethanol final concentration of 18.9% and a calcium chloride concentration of 5.7 mM was used in the reaction chamber 26. When the thrombin has been diluted 1 to 1.5 with water, the clot time has been extended to just less than 30 seconds, and has a life span of up to 150 minutes.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A method for extracting autologous thrombin from a patient, the steps consisting of:
   obtaining a blood product from the patient;
   sequestering plasma from the blood product;
   adding ethanol to the plasma to prepare a solution containing prothrombin, wherein ethanol is present in the solution at a concentration between about 8% and about 20% volume per unit volume;
   converting the prothrombin in the solution to thrombin;
   filtering the thrombin to remove particulate matter; and
   applying the thrombin to the patient.

2. The method of claim 1 further including the step of mixing the thrombin with clotting proteins to form a fibrin clot, but first altering time required for the thrombin to convert fibrinogen to a fibrin clot.

3. The method of claim 2 wherein altering time required for the thrombin to convert fibrinogen to a fibrin clot includes diluting the thrombin with saline.

4. The method of claim 3 including filtering the plasma to separate included particles by weight, size and protein binding.

5. The method of claim 2 wherein altering time required for the thrombin to convert fibrinogen to a fibrin clot includes adding a source of calcium ions to the solution.

6. The method of claim 2 wherein altering time required for the thrombin to convert fibrinogen to a fibrin clot includes adding $CaCl_2$ to the solution.

7. The method of claim 2 wherein altering time required for the thrombin to convert fibrinogen to a fibrin clot includes adding saline to the solution.

8. The method of claim 2 wherein altering time required for the thrombin to convert fibrinogen to a fibrin clot includes adding sterile water to the solution.

9. The method of claim 2 wherein altering time required for the thrombin to convert fibrinogen to a fibrin clot includes changing concentration of the ethanol.

10. The method of claim 1 wherein the converting step includes adding $CaCl_2$ to the solution.

11. The method of claim 10 including centrifuging the blood product for obtaining plasma.

12. The method of claim 1 wherein ethanol is present in the solution at a concentration of about 18.9% volume per unit volume.

13. The method of claim 1 wherein the time required to extract the thrombin is between about 30 minutes and about 75 minutes.

14. The method of claim 10 wherein $CaCl_2$ is present in the solution at a concentration between about 4.5 mM and about 23.0 mM by volume.

15. The method of claim 14 wherein $CaCl_2$ is present in the solution at a concentration of about 5.7 mM by volume.

16. The method of claim 10 wherein the converting step further includes agitating the solution after adding $CaCl_2$ to the solution.

17. A method for extracting and then dispensing thrombin, the steps consisting of:
   taking whole blood from a person,
   sequestering prothrombin from the whole blood by addition of ethanol, wherein ethanol is present at a concentration between about 8% and about 20% volume per unit volume,
   converting the prothrombin to thrombin,
   loading the thrombin into a syringe, and
   using the syringe to dispense the thrombin to stem blood flow.

18. The method of claim 17 including loading clotting proteins into another syringe and dispensing the clotting proteins concurrently with the thrombin.

19. A method for extracting thrombin from one person, the steps consisting of:
   adding ethanol to sequester prothrombin from plasma taken from one person, wherein ethanol is present at a concentration between about 8% and about 20% volume per unit volume,
   converting the prothrombin to thrombin, and
   removing particulate material from the thrombin.

20. The method of claim 19 further including diluting the thrombin to alter time required for the thrombin to convert fibrinogen to a fibrin clot.

21. The method of claim 20 including adding a source of calcium ions to the thrombin to alter time required for the thrombin to convert fibrinogen to a fibrin clot.

22. The method of claim 21 including adding $CaCl_2$ to the thrombin to alter time required for the thrombin to convert fibrinogen to a fibrin clot.

23. The method of claim 20 including adding saline to the thrombin to alter time required for the thrombin to convert fibrinogen to a fibrin clot.

24. The method of claim 20 including adding sterile water to the thrombin to alter time required for the thrombin to convert fibrinogen to a fibrin clot.

25. The method of claim 19 wherein ethanol is present at a concentration of about 18.9% volume per unit volume.

26. The method of claim 19 wherein the time required to extract the thrombin is between about 30 minutes and about 75 minutes.

27. The method of claim 19 wherein the time required to extract the thrombin is less than about one hour and greater than zero minutes.

28. The method of claim 19 wherein the converting step includes adding $CaCl_2$.

29. A method for extracting thrombin from one person, the steps consisting of:

taking whole blood from one person, obtaining plasma from the whole blood, adding ethanol to the plasma to prepare a solution containing prothrombin, wherein ethanol is present in the solution at a concentration between about 8% and about 20% volume per unit volume, converting the prothrombin to thrombin, and sequestering the thrombin.

30. The method of claim 29 further including the step of mixing the thrombin with clotting proteins to form a fibrin clot, but first altering time required for the thrombin to convert fibrinogen to a fibrin clot to a time of between about two seconds and about five seconds.

31. The method of claim 30 wherein altering time required for the thrombin to convert fibrinogen to a fibrin clot includes adding a source of calcium ions to the solution.

32. The method of claim 31 wherein altering time required for the thrombin to convert fibrinogen to a fibrin clot includes adding $CaCl_2$ to the solution.

33. The method of claim 30 wherein altering time required for the thrombin to convert fibrinogen to a fibrin clot includes adding saline to the solution.

34. The method of claim 30 wherein altering time required for the thrombin to convert fibrinogen to a fibrin clot includes adding sterile water to the solution.

35. The method of claim 29 including making the thrombin stable for a period of time between about 15 minutes and about 360 minutes.

36. The method of claim 35 including adding a source of calcium ions to the solution to alter time required for the thrombin to convert fibrinogen to a fibrin clot.

37. The method of claim 36 including adding $CaCl_2$ to the solution to alter time required for the thrombin to convert fibrinogen to a fibrin clot.

38. The method of claim 35 including adding saline to the solution to alter time required for the thrombin to convert fibrinogen to a fibrin clot.

39. The method of claim 35 including adding sterile water to the solution to alter time required for the thrombin to convert fibrinogen to a fibrin clot.

40. The method of claim 29 wherein ethanol is present in the solution at a concentration of about 18.9% volume per unit volume.

41. The method of claim 29 wherein the time required to extract the thrombin is between about 30 minutes and about 75 minutes.

42. The method of claim 29 wherein the time required to extract the thrombin is less than about one hour and greater than zero minutes.

43. The method of claim 29 wherein the converting step includes adding $CaCl_2$ to the solution.

44. A method for extracting autologous thrombin from a patient, the steps consisting essentially of:

obtaining a blood product from the patient;

sequestering plasma from the blood product;

adding ethanol to the plasma to prepare a solution containing prothrombin, wherein ethanol is present in the solution at a concentration between about 8% and about 20% volume per unit volume;

converting the prothrombin in the solution to thrombin;

filtering the thrombin to remove particulate matter; and applying the thrombin to the patient.

45. The method of claim 44 wherein ethanol is present in the solution at a concentration of about 18.9% volume per unit volume.

46. The method of claim 44 wherein the time required to extract the autologous thrombin is between about 30 minutes and about 75 minutes.

47. The method of claim 44 further including the step of mixing the thrombin with clotting proteins to form a fibrin clot, but first altering time required for the thrombin to convert fibrinogen to a fibrin clot.

48. The method of claim 47 wherein altering time required for the thrombin to convert fibrinogen to a fibrin clot includes changing the concentration of the ethanol.

49. The method of claim 47 wherein altering time required for the thrombin to convert fibrinogen to a fibrin clot includes diluting the thrombin with saline.

50. The method of claim 44 wherein the converting step includes adding $CaCl_2$ to the solution.

51. The method of claim 50 wherein $CaCl_2$ is present in the solution at a concentration between about 4.5 mM and about 23.0 mM by volume.

52. The method of claim 51 wherein $CaCl_2$ is present in the solution at a concentration of about 5.7 mM by volume.

53. The method of claim 50 wherein the converting step further includes agitating the solution after the addition of the $CaCl_2$ to the solution.

54. The method of claim 50 including centrifuging the blood product for obtaining plasma.

55. A method for extracting and then dispensing thrombin, the steps consisting essentially of:

taking whole blood from a person, sequestering prothrombin from the whole blood by addition of ethanol, wherein ethanol is present at a concentration between about 8% and about 20% volume per unit volume, converting the prothrombin to thrombin, loading the thrombin into a syringe, and using the syringe to dispense the thrombin to stem blood flow.

56. The method of claim 55 including loading clotting proteins into another syringe and dispensing the clotting proteins concurrently with the thrombin.

57. A method for extracting thrombin from one person, the steps consisting essentially of:

adding ethanol to sequester prothrombin from plasma taken from one person, wherein ethanol is present at a concentration between about 8% and about 20% volume per unit volume, converting the prothrombin to thrombin, and removing particulate material from the thrombin.

58. The method of claim 57 wherein ethanol is present at a concentration of about 18.9% volume per unit volume.

59. The method of claim 57 wherein the time required to extract the thrombin is between about 30 minutes and about 75 minutes.

60. The method of claim 57 wherein the time required to extract the thrombin is less than about one hour and greater than zero minutes.

61. The method of claim 57 wherein the converting step includes adding $CaCl_2$.

62. The method of claim 57 further including diluting the thrombin to alter time required for the thrombin to convert fibrinogen to a fibrin clot.

63. The method of claim 62 including adding a source of calcium ions to alter time required for the thrombin to convert fibrinogen to a fibrin clot.

64. The method of claim 63 including adding $CaCl_2$ to alter time required for the thrombin to convert fibrinogen to a fibrin clot.

65. The method of claim 62 including adding saline to alter time required for the thrombin to convert fibrinogen to a fibrin clot.

66. The method of claim 62 including adding sterile water to alter time required for the thrombin to convert fibrinogen to a fibrin clot.

67. A method for extracting thrombin from one person, the steps consisting essentially of:
  taking whole blood from one person,
  obtaining plasma from the whole blood,
  adding ethanol to the plasma to prepare a solution containing prothrombin, wherein ethanol is present in the solution at a concentration between about 8% and about 20% per volume per unit volume,
  converting the prothrombin to thrombin, and
  sequestering the thrombin.

68. The method of claim 67 wherein ethanol is present in the solution at a concentration of about 18.9% volume per unit volume.

69. The method of claim 67 wherein the time required to extract the thrombin is between about 30 minutes and about 75 minutes.

70. The method of claim 67 wherein the time required to extract the thrombin is less than about one hour and greater than zero minutes.

71. The method of claim 67 wherein the converting step includes adding $CaCl_2$ to the solution.

72. The method of claim 67 further including the step of mixing the thrombin with clotting proteins to form a fibrin clot, but first altering time required for the thrombin to convert fibrinogen to a fibrin clot to a time of between about two seconds and about five seconds.

73. The method of claim 72 wherein altering time required for the thrombin to convert fibrinogen to a fibrin clot includes adding a source of calcium ions to the solution.

74. The method of claim 73 wherein altering time required for the thrombin to convert fibrinogen to a fibrin clot includes adding $CaCl_2$ to the solution.

75. The method of claim 72 wherein altering time required for the thrombin to convert fibrinogen to a fibrin clot includes adding saline to the solution.

76. The method of claim 72 wherein altering time required for the thrombin to convert fibrinogen to a fibrin clot includes adding sterile water to the solution.

77. The method of claim 67 including making the thrombin stable for a period of time between about 15 minutes and about 360 minutes.

78. The method of claim 77 including adding a source of calcium ions to the solution to alter time required for the thrombin to convert fibrinogen to a fibrin clot.

79. The method of claim 78 including adding $CaCl_2$ to the solution to alter time required for the thrombin to convert fibrinogen to a fibrin clot.

80. The method of claim 77 including adding saline to the solution to alter time required for the thrombin to convert fibrinogen to a fibrin clot.

81. The method of claim 77 including adding sterile water to the solution to alter time required for the thrombin to convert fibrinogen to a fibrin clot.

82. A method for extracting thrombin, the steps consisting essentially of:
  taking whole blood from a person,
  obtaining plasma from the whole blood,
  adding ethanol to the plasma to prepare a solution containing prothrombin, wherein ethanol is present in the solution at a concentration between about 8% and about 20% per volume per unit volume,
  converting the prothrombin to thrombin, and
  sequestering the thrombin.

83. The method of claim 82 wherein ethanol is present in the solution at a concentration of about 18.9% volume per unit volume.

84. The method of claim 82 wherein the time required to extract the thrombin is between about 30 minutes and about 75 minutes.

85. The method of claim 82 wherein the time required to extract thrombin is less than about one hour and greater than zero minutes.

86. The method of claim 82 wherein the converting step includes adding $CaCl_2$ to the solution.

87. The method of claim 82 further including the step of mixing the thrombin with clotting proteins to form a fibrin clot but first altering time required for the thrombin to convert fibrinogen to a fibrin clot to a time of between about two seconds and about five seconds.

88. The method of claim 87 wherein altering time required for the thrombin to convert fibrinogen to a fibrin clot includes adding a source of calcium ions to the solution.

89. The method of claim 88 wherein altering time required for the thrombin to convert fibrinogen to a fibrin clot includes adding $CaCl_2$ to the solution.

90. The method of claim 87 wherein altering time required for the thrombin to convert fibrinogen to a fibrin clot includes adding saline to the solution.

91. The method of claim 87 wherein altering time required for the thrombin to convert fibrinogen to a fibrin clot includes adding sterile water to the solution.

92. The method of claim 82 including making the thrombin stable for a period of time between about 15 minutes and about 360 minutes.

93. The method of claim 92 including adding a source of calcium ions to the solution to alter time required for the thrombin to convert fibrinogen to a fibrin clot.

94. The method of claim 93 including adding $CaCl_2$ to the solution to alter time required for the thrombin to convert fibrinogen to a fibrin clot.

95. The method of claim 92 including adding saline to the solution to alter time required for the thrombin to convert fibrinogen to a fibrin clot.

96. The method of claim 92 including adding sterile water to the solution to alter time required for the thrombin to convert fibrinogen to a fibrin clot.

97. A method for extracting and then dispensing thrombin, the steps consisting of:
  taking whole blood from a person,
  sequestering prothrombin from the whole blood by addition of ethanol,
  converting the prothrombin to thrombin,
  making the thrombin stable for a period of time between about 15 minutes and about 360 minutes,
  loading the thrombin into a syringe, and
  the syringe to dispense the thrombin to stem blood flow.

98. A method for extracting thrombin from one person, the steps consisting of:

taking whole blood from one person, obtaining plasma from the whole blood, adding ethanol to the plasma to prepare a solution containing prothrombin, converting the prothrombin to thrombin, making the thrombin stable for a period of time between about 15 minutes and about 360 minutes, and sequestering the thrombin.

99. A method for extracting and then dispensing thrombin, the steps consisting essentially of:

taking whole blood from a person, sequestering prothrombin from the whole blood by addition of ethanol, converting the prothrombin to thrombin, making the thrombin stable for a period of time between about 15 minutes and about 360 minutes, loading the thrombin into a syringe, and using the syringe to dispense the thrombin to stem blood flow.

100. A method for generating thrombin from one person, the steps consisting essentially of:

taking whole blood from one person, obtaining plasma from the whole blood, adding ethanol to the plasma to prepare a solution containing prothrombin, converting the prothrombin to thrombin, making the thrombin stable for a period of time between about 15 minutes and about 360 minutes, and sequestering the thrombin.

101. A method for extracting thrombin, the steps consisting essentially of:

taking whole blood from a person, obtaining plasma from the whole blood, adding ethanol to the plasma to prepare a solution containing prothrombin, converting the prothrombin to thrombin, making the thrombin stable for a period of time between about 15 minutes and about 360 minutes, and sequestering the thrombin.

102. A method for extracting autologous thrombin from a patient, the steps consisting of:

obtaining a blood product from the patient;

sequestering plasma from the blood product;

adding ethanol to the plasma to prepare a solution containing prothrombin;

converting the prothrombin in the solution to thrombin;

filtering the thrombin to remove particulate matter; and applying the thrombin to the patient, wherein the time required to extract the autologous thrombin is between about 30 minutes and about 75 minutes.

103. A method for extracting and then dispensing thrombin, the steps consisting of:

taking whole blood from a person, sequestering prothrombin from the whole blood by addition of ethanol, converting the prothrombin to thrombin, loading the thrombin into a syringe, and using the syringe to dispense the thrombin to stem blood flow, wherein the time required to extract the thrombin is between about 30 minutes and about 75 minutes.

104. A method for extracting thrombin from one person, the steps consisting of:

adding ethanol to sequester prothrombin from plasma taken from one person, converting the prothrombin to thrombin, and removing particulate material from the thrombin, wherein the time required to extract the thrombin is between about 30 minutes and about 75 minutes.

105. A method for extracting thrombin from one person, the steps consisting of:

taking whole blood from one person, obtaining plasma from the whole blood, adding ethanol to the plasma to prepare a solution containing prothrombin, converting the prothrombin to thrombin; and sequestering the thrombin, wherein the time required to extract the thrombin is between about 30 minutes and about 75 minutes.

106. A method for extracting autologous thrombin from a patient, the steps consisting essentially of:

obtaining a blood product from the patient;

sequestering plasma from the blood product;

adding ethanol to the plasma to prepare a solution containing prothrombin;

converting the prothrombin in the solution to thrombin;

filtering the thrombin to remove particulate matter; and applying the thrombin to the patient, wherein the time required to extract the autologous thrombin is between about 30 minutes and about 75 minutes.

107. A method for extracting and then dispensing thrombin, the steps consisting essentially of:

taking whole blood from a person, sequestering prothrombin from the whole blood by addition of ethanol, converting the prothrombin to thrombin, loading the thrombin into a syringe, and using the syringe to dispense the thrombin to stem blood flow, wherein the time required to extract the thrombin is between about 30 minutes and about 5 minutes.

108. A method for extracting thrombin from one person, the steps consisting essentially of:

adding ethanol to sequester prothrombin from plasma taken from one person, converting the prothrombin to thrombin, and removing particulate material from the thrombin, wherein the time required to extract the thrombin is between about 30 minutes and about 75 minutes.

109. A method for extracting thrombin from one person, the steps consisting essentially of:

taking whole blood from one person, obtaining plasma from the whole blood, adding ethanol to the plasma to prepare a solution containing prothrombin, converting the prothrombin to thrombin, and sequestering the thrombin, wherein the time required to extract the thrombin is between about 30 minutes and about 75 minutes.

110. A method for extracting thrombin, the steps consisting essentially of:

taking whole blood from a person, obtaining plasma from the whole blood, adding ethanol to the plasma to prepare a solution containing prothrombin, converting the prothrombin to thrombin, and sequestering the thrombin.

111. A method for extracting autologous thrombin from a patient, the steps consisting of:

obtaining a blood product from the patient;

sequestering plasma from the blood product;

adding ethanol to the plasma to prepare a solution containing prothrombin, converting the prothrombin in the solution to thrombin;

filtering the thrombin to remove particulate matter;

applying the thrombin to the patient; and mixing the thrombin with clotting proteins to form a fibrin clot, but first altering time required for the thrombin to convert fibrinogen to a fibrin clot to a time of between about two seconds and about five seconds by adding an altering agent selected from the group including calcium ion sources, $CaCl_2$, saline, and sterile water.

112. A method for extracting and then dispensing thrombin, the steps consisting of:

taking whole blood from a person, sequestering prothrombin from the whole blood by addition of ethanol, converting the prothrombin to thrombin, loading the thrombin into a syringe, using the syringe to dispense the thrombin to stem blood flow, and mixing the thrombin with clotting proteins to form a fibrin clot, but first altering time required for the thrombin to convert fibrinogen to a fibrin clot to a time of between about two seconds and about five seconds by adding an altering agent selected from the group including calcium ion sources, $CaCl_2$, saline, and sterile water.

113. A method for extracting thrombin from one person, the steps consisting of:

adding ethanol to sequester prothrombin from plasma taken from one person, converting the prothrombin to thrombin, removing particulate material from the thrombin, and mixing the thrombin with clotting proteins to form a fibrin clot, but first altering time required for the thrombin to convert fibrinogen to a fibrin clot to a time of between about two seconds and about five seconds by adding an altering agent selected from the group including calcium ion sources, $CaCl_2$, saline, and sterile water.

114. A method for extracting thrombin from one person, the steps consisting of:

taking whole blood from one person, obtaining plasma from the whole blood, adding ethanol to the plasma to prepare a solution containing prothrombin, converting the prothrombin to thrombin, sequestering the thrombin, and mixing the thrombin with clotting proteins to form a fibrin clot, but first altering time required for the thrombin to convert fibrinogen to a fibrin clot to a time of between about two seconds and about five seconds by adding an altering agent selected from the group including calcium ion sources, $CaCl_2$, saline, and sterile water.

115. A method for extracting autologous thrombin from a patient, the steps consisting essentially of:

obtaining a blood product from the patient;

sequestering plasma from the blood product;

adding ethanol to the plasma to prepare a solution containing prothrombin;

converting the prothrombin in the solution to thrombin;

filtering the thrombin to remove particulate matter;

applying the thrombin to the patient; and mixing the thrombin with clotting proteins to form a fibrin clot, but first altering time required for the thrombin to convert fibrinogen to a fibrin clot to a time of between about two seconds and about five seconds by adding an altering agent selected from the group including calcium ion sources, $CaCl_2$, saline, and sterile water.

116. A method for extracting and then dispensing thrombin, the steps consisting essentially of:

taking whole blood from a person, sequestering prothrombin from the whole blood by addition of ethanol, converting the prothrombin to thrombin, loading the thrombin into a syringe, using the syringe to dispense the thrombin to stem blood flow, and mixing the thrombin with clotting proteins to form a fibrin clot, but first altering time required for the thrombin to convert fibrinogen to a fibrin clot to a time of between about two seconds and about five seconds by adding an altering agent selected from the group including calcium ion sources, $CaCl_2$, saline, and sterile water.

117. A method for extracting thrombin from one person, the steps consisting essentially of:

adding ethanol to sequester prothrombin from plasma taken from one person, converting the prothrombin to thrombin, removing particulate material from the thrombin, and mixing the thrombin with clotting proteins to form a fibrin clot, but first altering time required for the thrombin to convert fibrinogen to a fibrin clot to a time of between about two seconds and about five seconds by adding an altering agent selected from the group including calcium ion sources, $CaCl_2$, saline, and sterile water.

118. A method for extracting thrombin from one person, the steps consisting essentially of:

taking whole blood from one person, obtaining plasma from the whole blood, adding ethanol to the plasma to prepare a solution containing prothrombin, converting the prothrombin to thrombin, sequestering the thrombin, and mixing the thrombin with clotting proteins to form a fibrin clot, but first altering time required for the thrombin to convert fibrinogen to a fibrin clot to a time of between about two seconds and about five seconds by adding an altering agent selected from the group including calcium ion sources, $CaCl_2$, saline, and sterile water.

119. A method for extracting thrombin, the steps consisting essentially of:

taking whole blood from a person, obtaining plasma from the whole blood, adding ethanol to the plasma to prepare a solution containing prothrombin, converting the prothrombin to thrombin, sequestering the thrombin, and mixing the thrombin with clotting proteins to form a fibrin clot, but first altering time required for the thrombin to convert fibrinogen to a fibrin clot to a time of between about two seconds and about five seconds by adding an altering agent selected from the group including calcium ion sources, $CaCl_2$, saline, and sterile water.

* * * * *